(12) United States Patent
Bader

(10) Patent No.: US 9,101,692 B2
(45) Date of Patent: Aug. 11, 2015

(54) RAPID PREPARATION AND USE OF ENGINEERED TISSUE AND SCAFFOLDS AS INDIVIDUAL IMPLANTS

(76) Inventor: Augustinus Bader, Parthenstein-Klinga (DE)

( * ) Notice: Subject to any disclaimer, the term of this patent is extended or adjusted under 35 U.S.C. 154(b) by 417 days.

(21) Appl. No.: 13/141,884

(22) PCT Filed: Dec. 23, 2009

(86) PCT No.: PCT/EP2009/009265
§ 371 (c)(1),
(2), (4) Date: Jul. 11, 2011

(87) PCT Pub. No.: WO2010/072417
PCT Pub. Date: Jul. 1, 2010

(65) Prior Publication Data
US 2011/0256204 A1    Oct. 20, 2011

(30) Foreign Application Priority Data

Dec. 24, 2008  (EP) ..................................... 08022449

(51) Int. Cl.
*A61L 27/00* (2006.01)
*A61L 27/38* (2006.01)

(52) U.S. Cl.
CPC ......... *A61L 27/3834* (2013.01); *A61L 27/3895* (2013.01)

(58) Field of Classification Search
None
See application file for complete search history.

(56) References Cited

U.S. PATENT DOCUMENTS

2008/0031850 A1    2/2008  Bader

FOREIGN PATENT DOCUMENTS

DE        102 27 611  A1    1/2004

OTHER PUBLICATIONS

Becerra et al., Autologous human-derived bone marrow cells exposed to a novel TGF-beta1 fusion protein for the treatment of critically sized tibial defect, Regen. Med. 1(2):267-78, 2006.*
McCullen et al. (2011) In vivo tissue engineering of musculoskeletal tissues. Current Opinion in Biotechnology 22: 715-720.*
Ikada et al. "Challenges in tissue engineering." J R Soc Interface. (Oct. 2006); 3(10): pp. 589-601.*
Onuki et al. "A Review of the Biocompatibility of Implantable Devices: Current Challenges to Overcome Foreign Body Response." Journal of Diabetes Science and Technology (Nov. 2008); 2(6): pp. 1003-1015.*

* cited by examiner

*Primary Examiner* — Thaian N Ton
*Assistant Examiner* — Titilayo Moloye
(74) *Attorney, Agent, or Firm* — Davis & Bujold, P.L.L.C; Michael J. Bujold

(57) ABSTRACT

Methods, technical apparatus and compositions to achieve short term processing for the manufacture of a graft or a transplant in the form of a scaffold that can be used to treat or to heal injuries and traumas of a great diversity of tissues and organs in a central or peripheral location of the human or an animal body. Tissue regeneration by way of stem cells and different specific tissue and organ repair promoting factors that activate the endogenous or exogenous stem cells to differentiate to specific tissue cells thus reconstituting the original microenvironment of the cell damaged by the injury.

17 Claims, 10 Drawing Sheets

Figure 5 (a) (b):
(a)
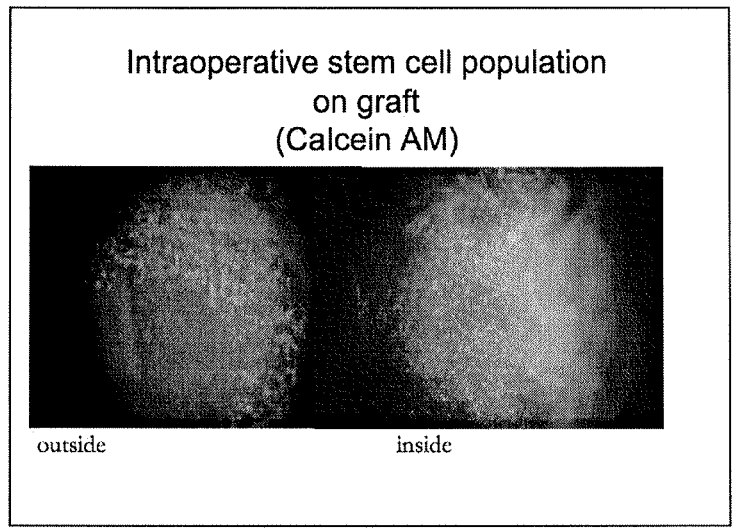
(b)
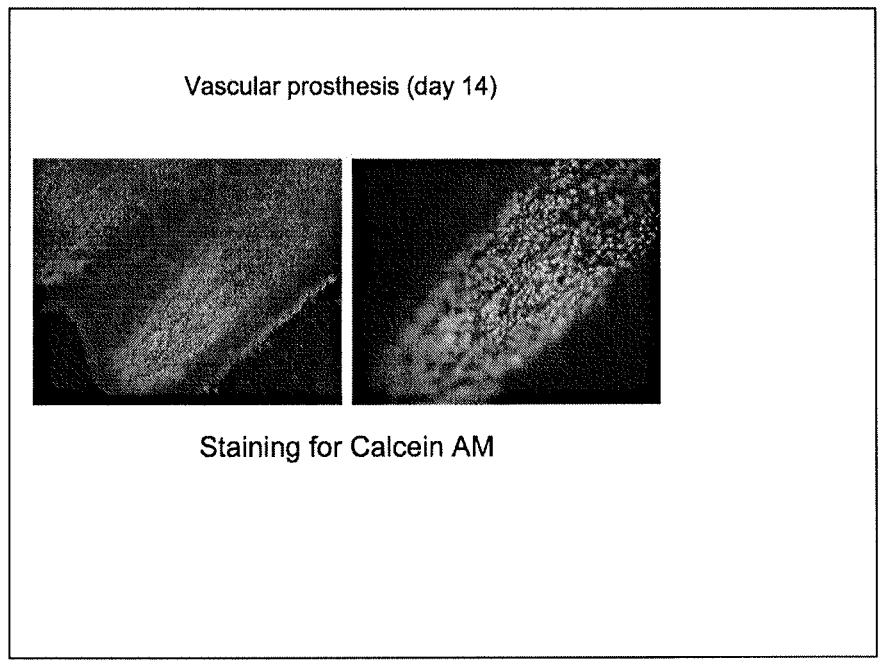

Figure 5 (c) (d):
(c)
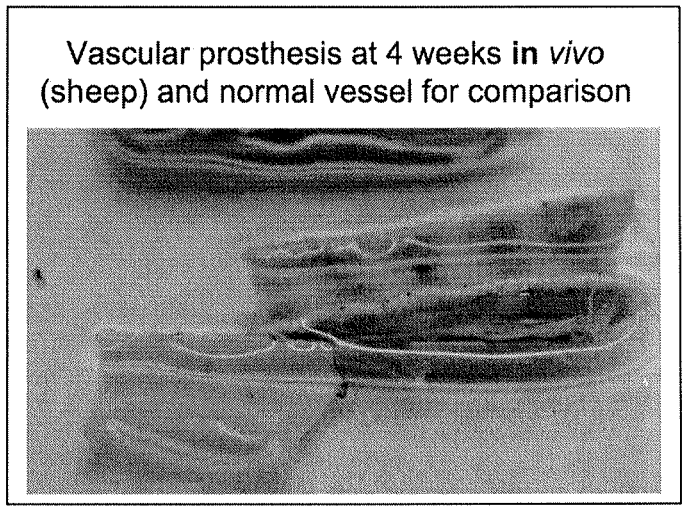
(d)
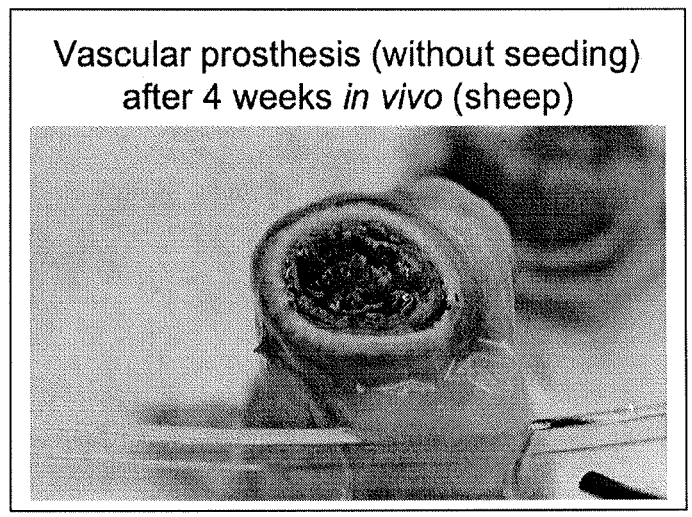

Figure 5 (e) (f):
(e)
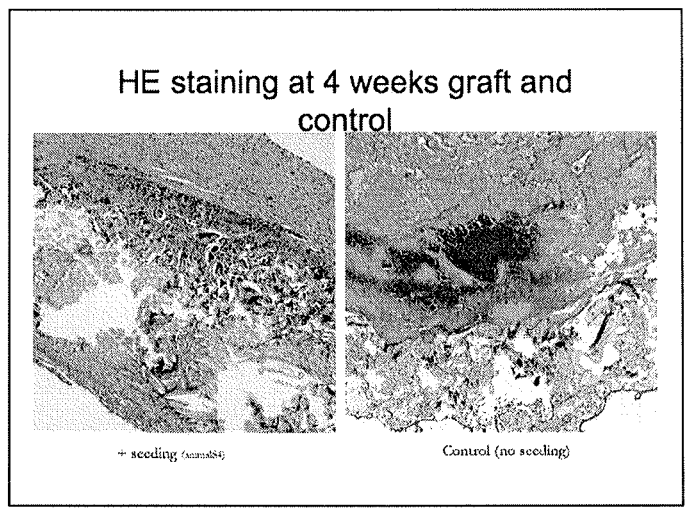
(f)
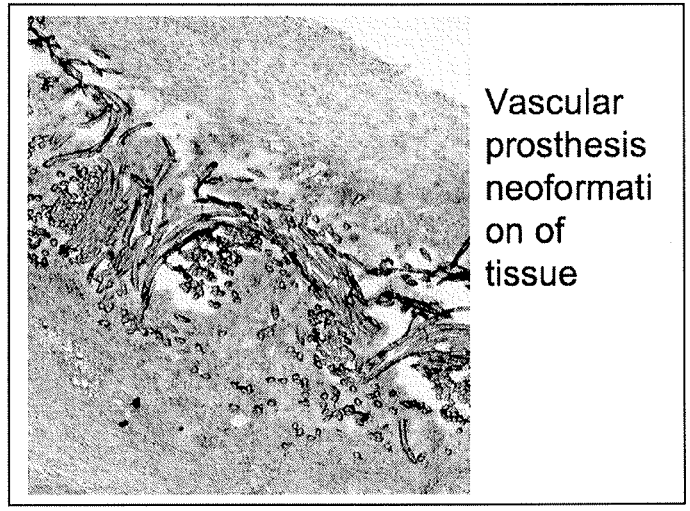

Figure 5 (g) (h):
(g)
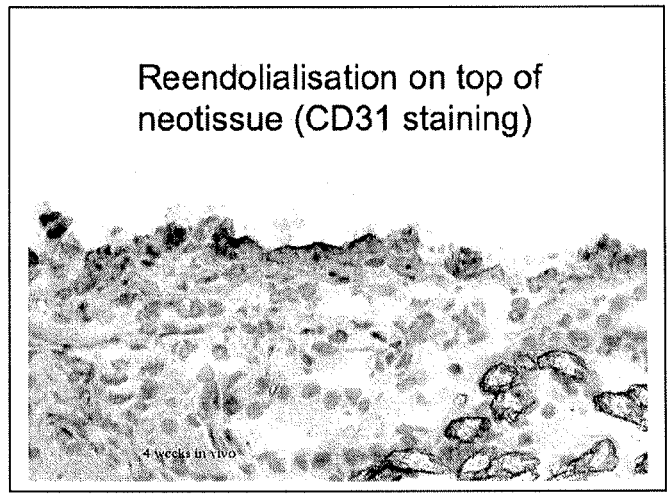
(h)
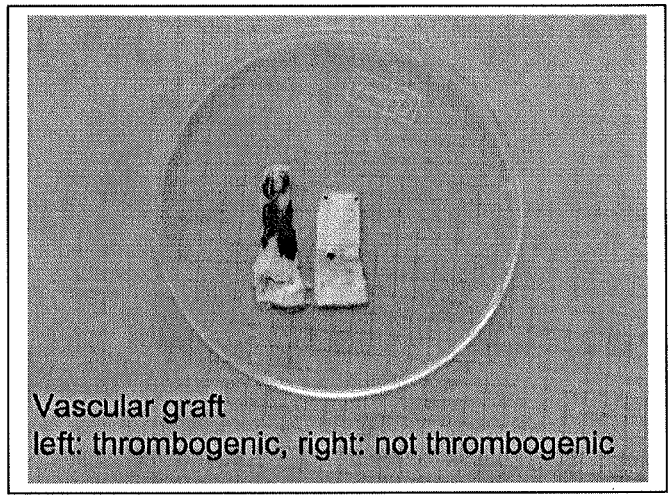
Figure 6:
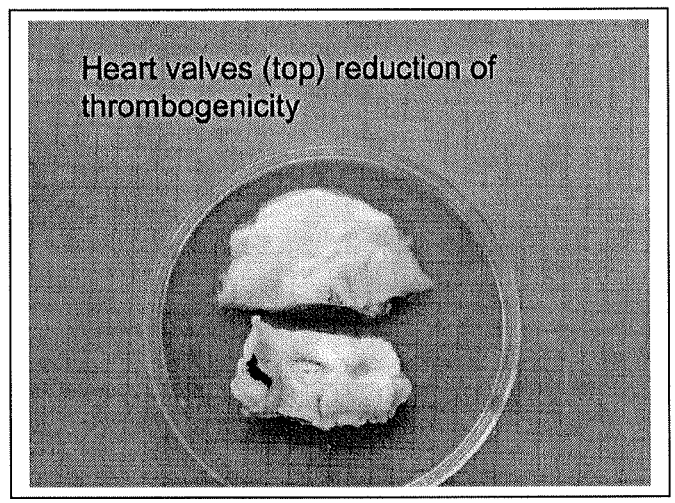

Figure 7 (a) (b):
(a)
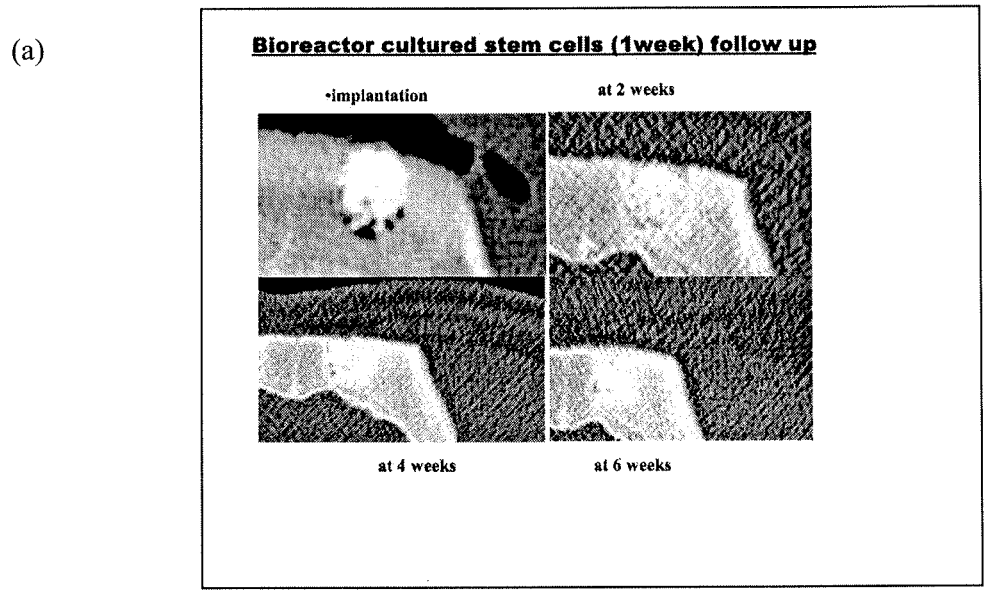
(b)
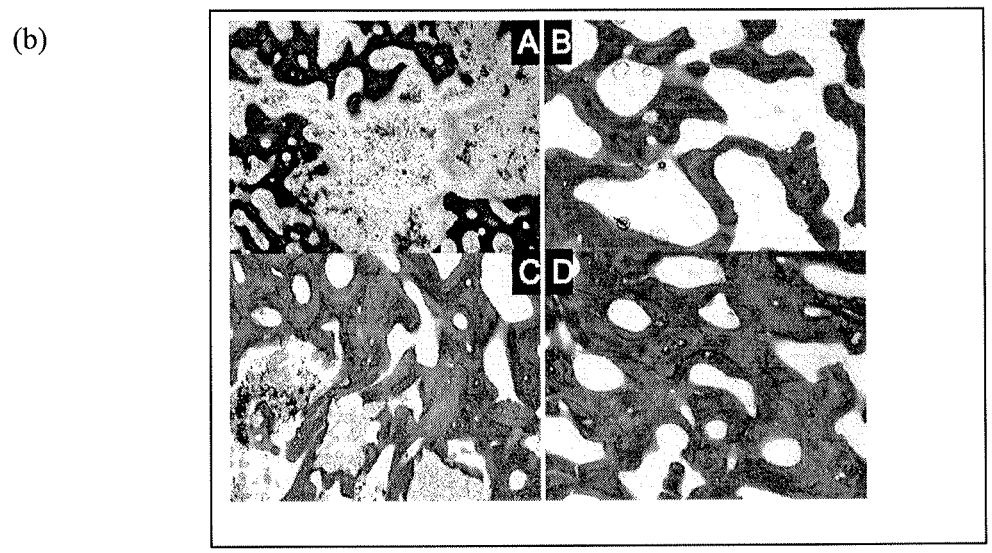

Figure 8 (a) (b):
(a)
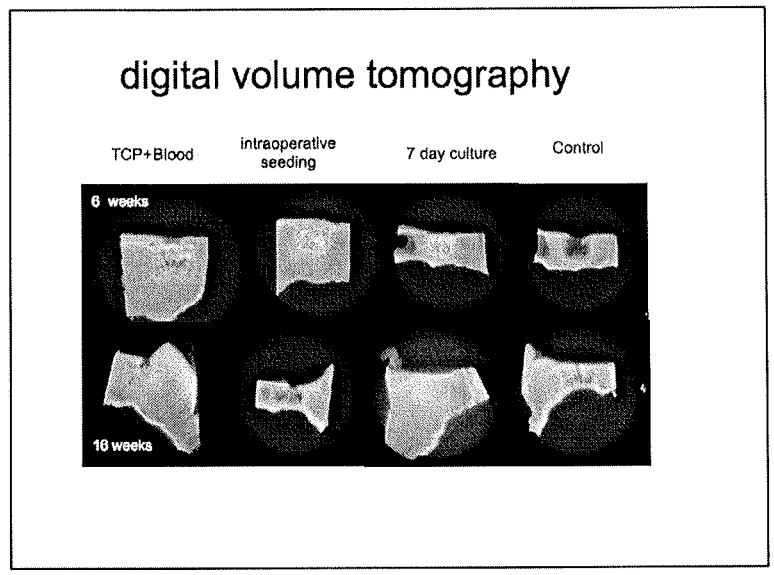
(b)
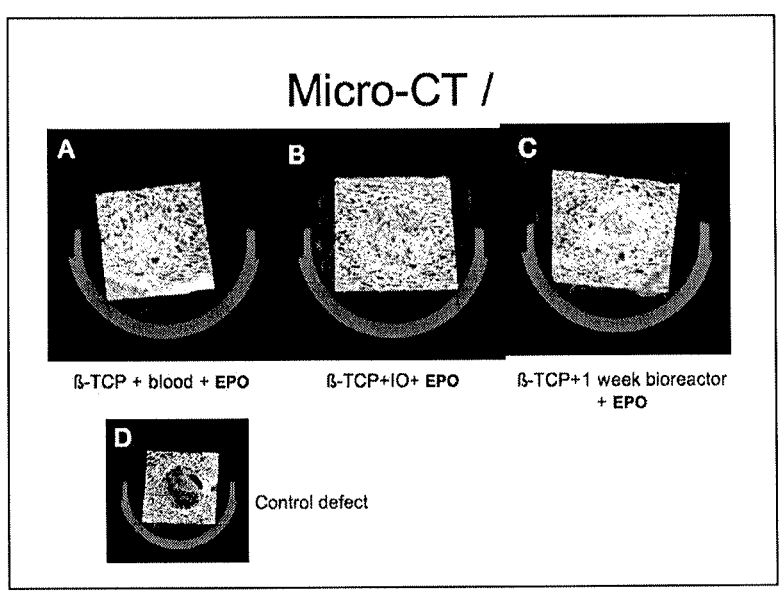

Figure 9 (a) (b) (c):
(a)
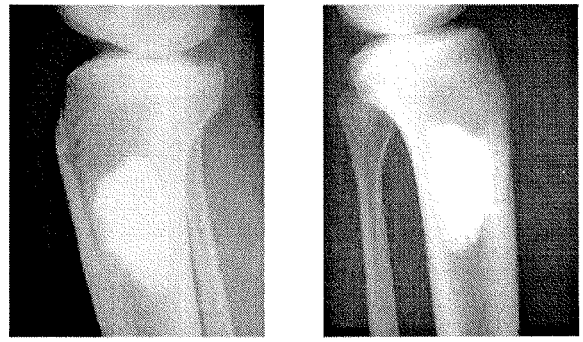
(b)
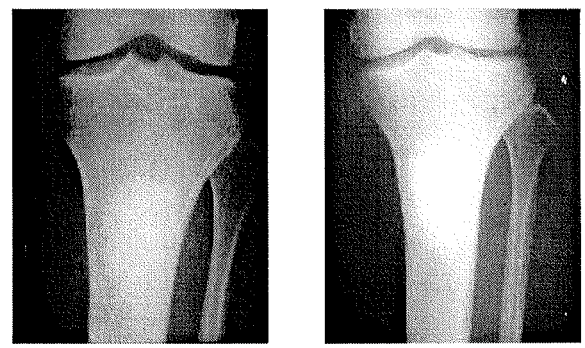
(c)
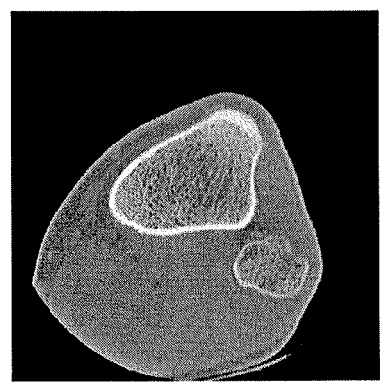

RAPID PREPARATION AND USE OF ENGINEERED TISSUE AND SCAFFOLDS AS INDIVIDUAL IMPLANTS

This application is a National Stage completion of PCT/EP2009/009265 filed Dec. 23, 2009, which claims priority from European patent application serial no. 08022449.6 filed Dec. 24, 2008.

FIELD OF THE INVENTION

The present invention relates to methods, technical apparatus and compositions to achieve short term processing for the manufacture of a "smart" graft or transplant in form of a scaffold that can be used to treat or to heal injuries and traumas of a great diversity of tissues and organs in a central or peripheral location of the human or animal body. The invention specifically relates to tissue regeneration by means of stem cells and different specific tissue and organ repair promoting factors that activate said endogenous or exogenous stem cells to differentiate to specific tissue cells thus reconstituting the original microenvironment of the cell damaged by the injury. The invention also relates to a time scale of processing that is so short that it can be done within a matter of minutes including stem cell preparation and stem cell integration, stem cell activation and commitment. Depending upon the size of the defect the stem cells will be added for large defects but also sufficiently recruited locally in smaller defects. A combination of both cell recruitment options is possible to ensure continued regeneration over a period of several weeks inside the body until complete restoration of tissue morphology and function has resulted.

In particular, the present invention relates to a novel method capable of initiating an excellent stem cell preparation process, that is so short that it applies to a time frame of a few seconds to several minutes.

The method is based on the concept of extracorporeal triggering of a niche formation that allows stem cells to be guided for remodeling ex vivo/in vivo and in situ without the need for any in vitro expansion or protracted culture processes. This novel method allows to generate templates that will remodel spontaneously into the targeted tissue of choice after completion of the extracorporeal processes. The invention is directed to almost all kinds of human or animal tissue.

The invention relates finally also to compositions and formulation or scaffolds coated with said compositions comprising (i) stem cell preparations, (ii) erythropoietin (EPO) and (ii) factors that promote differentiation of stem cells, (iv) factors that increase availability of stem cells, and optionally (v) factors which are usually present in the environment of a local trauma.

The invention can be used for rapid and safe preparation of individually engineered grafts, transplants or implants preferably in form of a scaffold for rapid, high quality and economical tissue regeneration.

BACKGROUND OF THE INVENTION

Tissue engineering of implants is a long and risky process with respect to maintaining sterility, which implies procurement of cells from the donor, transfer of the cells to a laboratory and manipulation of such cells to initiate expansion and/or differentiation. Following the expansion period cells are frequently removed from a temporary attachment substrate by i.e. trypsinisation and thereafter transferred onto a scaffold and again cultured on this scaffold. This process therefore requires often not only days but weeks to be effective.

The rapid and correct manufacturing of complex 3D grafts is presently not known in the art. It is fundamental and indeed contradictory to current teaching, which focuses on cell technologies to expand and differentiate cells to trigger commitment in vitro and by seeding them thereafter onto scaffolds or growing them on these scaffolds directly. It is expected that those cells differentiate in vitro. This process often requires at least 1-2 weeks in average or even more.

A second line of teaching uses injecting methods for undifferentiated stem cells from bone marrow or blood or crude bone marrow as a form of cell therapy intra-operatively directly into a tissue including e.g. the heart muscle. For the repair of spinal injury cells were either cultured for expansion or from specific sources such as the nose or embryonic origin. The latter have the risk to go into transformation or tumor formation. The nose derived cells represent a rather infectious environment for harvesting and could not convince clinically as a generic solution. Bone marrow derived cells are under investigation.

A further alternative is de novo tissue regeneration. It was expected that the local environment will eventually help to differentiate these cells. Examining the receiving environment more closely it is found that the cells do not differentiate into e.g. heart muscle cells after injection into the heart. In these instances no formation of muscle cells was reported at all. Instead a rather positive effect from the secretory activity of the transplanted stem cells for support of recovery was postulated. Overall effects in such studies was a 4% improvement of cardiac function only. This means that this microenvironment hypothesis does not achieve the goal of tissue de novo formation but has an adjuvant role only.

In another study expanded MSC were injected after expansion in vitro into a acellularized valve scaffold. During in vitro culture cells underwent a selection process that achieved to select cells that have a prominent stem cell character (stronger replication) and that may lead to a reduced inflammation in vitro.

So far it is not clear what roles cytokines may play in this context. However it is well known from prior art that molecules in vitro can be used to control multipotency and to induce differentiation and commitment to a specific tissue.

Wound healing is closely linked to inflammatory responses. After surgical implantation of an artificial trachea the speed and quality of local healing, survival and integration is crucial for graft take and the long term success of the implant.

During inflammation cytokines are released such as IL-6, IL-1 and TNF that sustain the inflammatory response. Inflammation nevertheless can be a two-edged sword, if inflammation is not terminated in due course due to insufficient remodelling of the implant scaffold.

Scaffold remodeling in tissue engineering was conceived of as a rather unknown process and triggering mechanisms were either obscure or clinically not feasible. Conventionally cells would have been seeded onto the material of choice and integration into this material was a process that was attributed to ideally cell expansion time and migratory penetration.

Fundamentally, there is a positive side to inflammation being a perquisite for healing that needs to be taken into consideration for biological-implant engineering.

The prior art does not provide adequate teaching on the controlling either of the microenvironment after transplantation of the graft for sustainable remodeling, differentiation of undifferentiated cells after transplantation and of stem cells sensing the wound zones and does not teach adequately the differentiation of transplanted cells after expanded in vitro to achieve true scar free healing.

Such pre-expansion has been shown to activate oncogenes. This is caused by the exposure to an artificial environment and possible also to repetition of proliferation cycles that do not underlie normal control mechanisms of wound repair and remodeling. This artificial situation of course is not coherent with the body's capacity for regeneration following wounding and injury. Stem cell activation in man and stem cell commitment requires a full control of proliferation, while at the same time preventing oncogene activation.

These requirements are considered to be mandatory and their disregard in conventional teaching can cause the most severe and deleterious drawbacks of the current technology of in vitro cellular processes that inevitably are not only rather complicated but also risky for these reasons.

The other alternative represents a mere injection of stem cells, which is on the other hand no solution since the receiving site of the cells is highly variable and not fully controllable from the cell and scaffold transplanter's side. In all cases reported so far stem cells were at a closer look not fully achieving their original goal of resulting in an appropriate de novo tissue formation.

Accordingly there is need for controlling multipotency of stem cells after transplantation and at the time of transplantation. Past teaching was focusing on controls of multipotency rather before transplantation. A need also exists to avoid cell culture processes that may attempt to control cell differentiation but exhibit artificial side conditions that are harmful to the cells and are also not economical.

It is a great problem in carrying out these prior methods with respect to the quality and functionality of the transplant. Accordingly, there is demand for a method of abolishing all these limitations. The present invention was made in order to overcome the problems described, and to provide a practical method to rapidly engineer airway tissue and valves and in general all tissues of the animal or human body.

SUMMARY OF THE INVENTION

To solve the problems of cell culture or "blind" transplantation of cells, the present invention provides a new method and approach for controlling stem cell differentiation, rapid preparatory process of implants ex vivo, and implantation of these pretreated implants in vivo by a surgeon at the same time.

This all can be achieved by selecting a specific target: the stem cell which is specifically treated according to the invention.

It was found that endogenous or exogenous stem cells or progenitor thereof can be activated in injured tissues and artificial or natural scaffolds by exposing them to the conditions of a natural microenvironment. It was found that this microenvironment is damaged when larger injuries occur. In such a situation the necessary cells and factors are missing in the local environment of the damaged tissue or have lost their activity or efficacy. According to the invention, this microenvironment can be retained if the tissue to be regenerated or repaired or the respective tissue scaffolds or matrices are exposed to the necessary cells and tissue repair supporting factors. In this situation also endogenous factors, such as cytokines or other inflammatory factors, which are usually secreted into the wound, may assist and promote this tissue repair process. According to the finding of the invention stem cells, preferably CD90 positive stem cells, play here an important role. However, these stem cells need to be activated with respect to their capability for specific differentiation in order to generate new specific tissue without scaring or other undesired effects.

Activation of stem cells in situ can be done according to the invention with several different factors which support the achievement of and retaining of the optimum microenvironment of injured tissue thus promoting improved differentiation and growth of regenerated locally specific tissue.

A first group of supporting factors as defined by the present invention are stem cells or progenitor cells thereof, which have the capability to differentiate into any type of tissue cells, including cells of neuronal and lymphatic tissue. These factors are called "cell factors". These stem cells or progenitor cells thereof can be assisted according to the invention by peripheral blood monocytes (PBMC), by CD90 positive cells, or by CD45 positive cells.

A second group of supporting factors acting in this way are factors which stimulate stem cells and accelerate remodeling of tissue cells. These factors are called "boosting factors". These factors are no growth factors as it is usually understood by a skilled artisan. The preferred boosting factor of the invention is erythropoietin (EPO)

A third group of supporting factors according to the invention are designated "commitment factors" which support the differentiation of stem cells. The preferred commitment factor for cartilage differentiation of the invention is the combined use of TGRβ.

A fourth group of supporting factors according to the invention increase the availability of stem cells, which means an increase of the number of stem cells both in the peripheral and local environment of a tissue injury, and are called "recruitment factors". The preferred recruitment factor of the invention is G-CSF.

A fifth group of supporting factors according to the invention are designated "permissive factors". These factors, such as cytokines, are usually already present in tissue with local trauma or are secreted endogenously during inflammation accompanied by a local tissue injury.

According to the finding of the invention the factors of the first, second, third and fourth group are mandatory according to the invention and must be delivered to the location of the tissue injury or to the scaffold provided for transplantation into the injured tissue by exogenous application. The permissive factors can be applied optionally.

According to the invention the transplantation of stem cells or the induction of endogenous stem cell activation is accompanied by an exposure to a portfolio of factors. None of those factors alone permits the completion of the circle of events leading to scar free healing and remodeling. However they are important additions to control the multipotency of the cells acting in a concerted action amongst each other.

The availability of those factors can be done in at least three variants: A) addition during the cell application or cell activation phase (e.g. as lyophilisate to avoid dilution of the stem cell bone marrow concentrate) B) Addition to the scaffold during the production phase. A preferred way is the integration during the production of scaffold and integration into the material. This may be done be e.g. addition to biological scaffolds during a lyophilization procedure of the factors together with the scaffold matrix (e.g. collagen, chitosan, blood and blood components) or during an electrospinning process, the advantage being an intricate formation and combination and a non-damaging way of use, good storage capability) C) use of an ideally autologous substitute. Many of these factors, especially the commitment factors occur in the healthy tissue. A technique of mincing small biopsies and distributing them into the stem cell coating into the stem cell concentrates is preferred. A combination with a platelet concentration, the mincing results (e.g. fragments from cartilage, meniscus, tendons, skin, heart, sphincter tissue, valve or aortic tissue and indeed any other tissue) represents an important triggering event and is a valuable alternative and/or an addition to the isolated use of individual factors. Not all of them are available clinically at this time and need further development for clinical applicability.

In a first aspect of the invention a natural or synthetic scaffold mimicking the injured specific tissue is used. This scaffold material serves as a copy which catalyzes the process that finally results in the matrix of the tissue to be generated. In a specific embodiment of the invention this scaffold material contains individual specific tissue to be generated taken by a biopsy from the patient suffering from an injury or a tissue defect. The scaffold is coated, or partially or selectively loaded with the above-specified factors (including "cell factors") in vitro or ex vivo. In a specific embodiment of the invention the treatment of the scaffold with factors and optionally individual specific tissue from the patient occurs intraoperative, that means in temporal conjunction with surgery of the patient. Preferably, the factors and/or the scaffolds are pretreated according to the invention before combining them.

In a second aspect of the invention the factors as specified above are brought directly to the injured or defect tissue in the patient without a separate artificial or natural scaffold pretreated with the specific combination of factors. In this case, the factors are preferably formulated as a gel or glue composition which is filled in the tissue defect or wound in order to seal it.

The main advantage of this approach is, that the need for stem cell expansion and predifferentiation before transplantation is abolished completely. In addition the best quality of the implant is achieved as measured by histology and function following remodelling. A further advantage is the site specific mode of action of the commitment factors, that avoid systemic side effects. According to this teaching it is the local presence of permissive factors that together with the exogenously administered boosting factors allow an extremely rapid graft preparation to be done. A further result of the invention is that the scaffold used is remodeled faster and more efficiently by 40-50% over a control that is prepared in a conventional manner.

In a preferable embodiment of the method stem cells are obtained during the same session or operation that is used for the implantation.

The invention is so fundamental that it allows to overcome evolutionary barriers with respect to speed, quality and size of defect repair and tissue replacement. It allows neotissue formation and repair in situations that cannot be repaired by the body and allows phenomena to be achieved that do not occur normally in the human or animal body. The fundamentality of the invention therefore opens all necessary applications for all human and animal tissues of all kinds, as it is focused on a basic platform technology that works with all tissues by inducing favoruble wound healing conditions in disease states that could otherwise not be repaired normally or artificially.

The fields of applications include all disease states with ischemica, inflammation and defects of such a size that they either cannot heal spontaneously or if a closure would occur it would result in a scar tissue. A scar tissue is an indication of low quality defect healing that cannot reassume normal or original tissue function. This is important for any tissue in the body.

The invention can be used to treat, for example, spinal cord injury or to be interponed to heal a disconnected, injured or traumatized nerve tissue in a central or peripheral location of the human or animal body. It relates to an autologous implant preparation, stem cell signalling to induce tissue remodelling of a specific graft, but not limited to these tissues as it may apply also to further neuronal tissue (nerves, spinal cord, brain stroke, brain trauma) skin, eye, cornea, muscle (heart, sphincter tissue, sceletal muscle, vascular tissue muscle), vascular system (veins, arteries, capillaries), skin, lymphatic tissue, bladder, urethra, penis, ovaries, to a trachea, a heart valve, a urological tissue, a bone or a cartilage substitute or all other tissues of the human body. The reason for this applicability is, that it functions as a concerted action of stem cell handling that allows to achieve repair as a coordinated interplay of cells, materials and signalling.

The following generic protocol forms according to the invention the basis to achieve a complete remodeling using a scaffold. This protocol is not limiting the invention: single steps can be repeated, amended, dropped, added, replaced, or carried out in different sequence, if necessary. Sequence step in the method of the present invention in combination with the apparatus (self contained production mobile unit, MU)

(i) preparation of the scaffold in a sterile manner. The material serves as a material for initiating a copy process that finally results in the matrix of the desired tissue to be generated The scaffold may be synthetic, such as a collagen fleece or from natural origin (e.g. a swine valve);

(ii) sterile collection and preparation of adult/mesenchymal stem cells ("cell factors") from suitable sources, such as peripheral blood or bone marrow, by concentration or buffy coat preparation;

(iii) sterile collection of peripheral blood derived monocytes (PBMC) by concentration or buffy coat preparation;

(iv) incubation of the stem cell concentrate with a boosting factor according to the invention, preferably EPO, thus obtaining pretreated stem cells.

(v) incubation of the natural or artificial scaffold with a boosting factor according to the invention, preferably EPO;

(vi) integration or injection of collected pretreated or optionally untreated stem cells into/onto the pretreated or optionally untreated scaffold in vitro/ex vivo in a diffuse or patterned form depending on the desired structure to be generated (e.g. cartilage, bone, valve or others). In tubular systems injection of the pretreated stem cells occur into/onto the areas underneath the superficial;

(vii) integration or injection (as specified under (vi)) additionally of tissue cells (e.g. epithelial cells) obtained by individual biopsy from the injured or defected patient's specific tissue to be regenerated, into/onto said scaffold;

(viii) incubation of said pretreated or optionally untreated scaffolds with a boosting factor (preferably EPO) and commitment factor (preferably TGFβ) and a recruitment factor (preferably G-CSF), or alternatively only with a commitment factor and a recruitment factor, optionally by means of a gel-like or glue-like composition/formulation comprising said factors;

(ix) incubation as specified under (viii) optionally additionally with a PBMC preparation;

(x) Preparation of tissue specific fragments (e.g. minced cartilage from the recipient, epithelium or others for co-coating of the implant.

(xi) Use of a bioreactor or closed device for inoculation and positioning or mixture of cells with the implant scaffold (eg. bone, valve, collagen fleece) for GMP and automation requirements if necessary.

(xii) providing the so-prepared scaffold to the surgeon for implantation into the injured or defected tissue location of the patient.

(xiii) Intraoperative and in situ coating of implants from the sites that are accessible to reduce loss of cells. Cell-gels are applied topically after induction of clotting in the stem-cell bone marrow concentrate. Cell gels contain one or more boosting, commitment and recruitment factor(s)

The steps (i)-(ix) are carried out according to the invention in a laminar air flow cabinet or respective bioreactor or closed device, preferably in temporal conjunction with surgery within 10-30 minutes without cell replication or interim transport needs (all done in the same operating theatre).

After implantation, it is preferred according to the teaching of this invention to treat the implanted scaffold with gel-like or glue-like compositions comprising preferably all factors: cell factors (stem cells), commitment factors, boosting factors, recruitment factors and optionally permissive factors as defined according to the invention. The composition are applied in situ above at all sites that are accessible to reduce loss of cells.

The method as described above creates a regenerative cascade that allows remodeling of in situ matrix or co-administered scaffolds. The injections/incorporations carried out with said gel or glue composition comprising cells and factors as described creates a depot slow release effect, which is effective during the in vivo healing process.

Injections (e.g. also without coadministration of cells into joints) create a regenerative cascade that allows remodelling of in situ matrix or coadministered scaffolds.

In a further and completely new aspect of the invention a method fully respecting sociological and regulatory prerequisites by providing a technology that dramatically accelerates the speed of preparation of the implant, intended for surgical implantation onto the patient. This concept follows the bionic principles of the human body (FIG. 1). The manufacturing of the graft should not require 2-3 weeks according the prior art teaching, but can be carried out within minutes less than one hour to make different kinds of desired tissue. The whole process is ideally done intraoperatively and therefore eliminates the need to send the respective cells to laboratories. This solves limitation of logistics, unnecessary anesthesia and costs including time that can be saved by this intraoperative implant engineering process. In the hands of the doctor treating the patient and not leaving the operating room, the process fully complies with current regulatory and quality requirements. Thus, the implant is not the particular product which is separately handled, but the process to make the implant as part of the therapy. This is the safest methodology existing with respect to avoiding transformation and infectious risks thereby providing increasing quality. The scaffold to be used according to the invention is able to react to remodeling stimuli and, preferably, it is prepared by using fully closed GMP compliant one-way devices as principally known and used in the art. This technology is characterized above all by the fact that in vitro cell replication is completely avoided by using and applying the above specified factors, which are: cell factors ("the cells"), boosting factors (preferably naturally occurring biological molecules, such as EPO or GH), commitment factors (preferably naturally occurring biological molecules, such as TGFβ, VEGF, hormones or vitamins), recruitment factors (preferably naturally occurring biological molecules, such as G-CSF, GM-CSF) and optionally permissive factors (preferably naturally occurring biological molecules, such as trauma cytokines). The result of this approach is fast, efficient and perfect remodeling of defect or injured tissue, that is 40-50% faster over respective approaches that do not use said stimulating supporting factors. The new bionic technology concept as presented herewith benefits from the innate mechanisms of specific wound repair using them as co-triggering events, and the body's capacity to formulate a site-specific response, independent from the type and location of a tissue.

One of the advantages of the invention is that the application of EPO to the scaffold is results in a faster expansion of endothelial and smooth muscle progenitor cells from the surrounding areas to populate the scaffold. The technique employed alternatively refers to intermingling normal target cell structure or tissue fragments into the stem cell preparation to enhance paracrine signalling.

Subject matter of the present invention is also a method for healing injured, traumatized or defected tissue in a patient, thereby achieving restitutio ad integrum, wherein healthy cells from the tissue to be treated serve as copy cells, the method comprising the steps:

(i) recruiting autologous stem cells obtained from the patient to be treated by withdrawal from bone marrow, blood or other tissues;

(ii) recruiting healthy surrounding or surviving cells as co-differentiating cells obtained from the defected, traumatized or injured tissue or the environment thereof, (iii) applying to the patient by intravenous, subcutaneous or topical administration a composition or formulation comprising (A) the stem cells of step (i), (B) the healthy tissue cells of step (ii) and (C) a preparation comprising (a) at least one factor that stimulates stem cells and accelerate remodeling of tissue cells, (b) at least one factor that is able to control and direct differentiation of said stem cells, and (c) at least one factor that increases the number of stem cells both in situ and in the peripheral circulation.

In summary the invention relates to the following topics:

An ex vivo intraoperative method for manufacturing an individually engineered implant based on a natural or synthetic scaffold serving as a copy matrix for the tissue to be generated as a result of a tissue defect or tissue injury in a patient, the method comprising the steps:

(i) providing a natural or synthetic scaffold as supporting matrix for the growth of tissue cells;

(ii) providing autologous stem cells obtained from the patient to be treated;

(iii) providing healthy cells as copy cells obtained by biopsy from the defected or injured tissue of the patient to be treated;

(iv) incubating the stem cell preparation of step (ii) with a composition comprising a factor which stimulates stem cells and accelerates remodeling of tissue cells;

(v) loading or injecting the cell preparation of step (iii) onto or into the scaffold matrix;

(vi) incubating the pretreated scaffold matrix of step (v) in the presence of the pretreated stem cell preparation of step (iv) together with a composition comprising (a) a native factor recruiting and increasing the availability of stem cells, (b) a native factor that promotes differentiation of stem cells or its progenitor cells, and (c) the factor of step (iv); and (vii) providing the so treated scaffold for implantation into the patient to be treated by a surgeon, wherein steps (iv)-(vi) are carried out under sterile conditions in a bioreactor chamber or a laminar air flow cabinet during a period of 10 to 30 minutes.

The method as specified above, wherein the autologous stem cell of step (ii) and/or the tissue copy cell preparation of step (iii) was pretreated with a composition comprising (a) a factor recruiting and increasing the availability of stem cells, (b) a factor that promotes differentiation of stem cells or its progenitor cells, and optionally (c) a factor which stimulates stem cells and accelerates remodeling of tissue cells.

The method as specified, wherein the factor that stimulates stem cells and accelerates remodeling of tissue cells is selected from the group consisting of EPO and hGH, and wherein the factor that recruits and increases the availability of stem cells is selected from the group consisting of G-CSF and GM-CSF, and wherein the factor that promotes differentiation of stem cells or its progenitor cells is selected from the group consisting of TGRβ, VEGF, vitamin C, and vitamin E.

The method as specified, wherein the factor that recruits and increases the availability of stem cells is G-CSF, the factor that promotes differentiation of stem cells or its progenitor cells is TGFβ, and the factor which stimulates stem cells and accelerates remodeling of tissue cells is EPO.

A method as specified, wherein the stem cells are obtained from bone marrow or peripheral blood of the patient to be treated, and preferably have not been expanded before by a separate process step.

A corresponding method, wherein the incubation step of step (vi) includes addition of autologous peripheral blood derived monocytes (PBMC).

A method as specified, wherein the steps (iv)-(vi) are carried out simultaneously with the prearrangement of the patient to the implantation of the scaffold into or onto the defected or injured tissue.

A method of any of the claims 1 to 11, wherein the different factors and/or the different cells as specified in any of the preceding claims are provided to the scaffold by a viscose gel-like or glue-like formulation or composition.

A use of a scaffold obtained by a method as specified, for the manufacture of an implant for healing injured or defected tissue, thereby achieving restitutio ad integrum.

A respective use, wherein a viscose, gel-like or glue-like formulation or composition of the different factors and/or cells as specified in any of the preceding claims is provided for intraoperative in situ treatment of the freshly implanted scaffold at all or some selected sites of the defected or injured tissue.

The use of a preparation or composition comprising
(i) freshly prepared non-expanded autologous stem cells,
(ii) a factor that stimulates stem cells and accelerates remodeling of tissue cells selected from the group consisting of EPO and hGH,
(iii) a factor which recruits and increases the availability of stem cells selected from the group consisting of G-CSF and GM-CSF, and
(iv) a factor that promotes differentiation of stem cells or its progenitor cells selected from the group consisting of TGFβ, VEGF, vitamin C, and vitamin E,
for the manufacture of a medicament for the treatment of injured or defected tissue in a patient without or together with an implanted specific cell growth supporting scaffold, thereby achieving restitutio ad integrum.

The use as specified, wherein the preparation or composition or the scaffold comprises additionally healthy cells from the defected or injured tissue of the patient to be treated serving as copy cells, and optionally autologous PBMC, said cells were preferably pretreated with EPO and/or G-CSF and/or TGFβ.

The use as specified, wherein the composition or preparation is provided in a viscose, gel-like or glue-like formulation, which is applied to or injected into the defected or injured tissue at all or some selected sites, wherein preferably said formulation consists of blood, plasma or bone marrow, bone marrow concentrate, which is applied to or injected into the defected or injured tissue at all or some selected sites and induced to polymerize by addition of Ca++ or thrombin or other suitable polymerizing compounds.

A corresponding use, wherein the scaffold was pretreated with healthy cells from the defected or injured tissue of the patient to be treated, and optionally with autologous PBMC, and/or wherein the stem cells were pretreated with EPO and/or hGH.

The use as specified, wherein in case that a scaffold is applied, the preparation, treating and pre-treating of respective cells is intraoperatively achieved simultaneously with the surgery in a rapid process within a few minutes less than one hour.

The use as specified, wherein in case that no scaffold is applied, the composition or formulation of respective cells and factors is provided for systemic administration by intravenous or subcutaneous administration, or if the tissue to be treated is available by direct topical administration.

A method of intraoperative preparing of autologues cells that induce, stimulate and promote differentiation and growth of tissue cells in defected or injured tissue by means of a natural or synthetic scaffold in a patient, while prearranging and treating the patient for implantation of said scaffold into said patient, wherein said cells are (a) autologous stem cells from bone marrow, tissue or blood of a patient suffering from a tissue defect, tissue trauma or tissue injury, and (b) healthy tissue cells as copy cells for coating the scaffold matrix to be implanted into the patient, the method comprising the steps:
(i) identifying the site of damage in the patient;
(ii) recruiting autologous stem cells from the patient to be treated by withdrawal from bone marrow, blood or other tissues;
(iii) recruiting autologous tissue cells from the patient to be treated by biopsy of healthy surrounding or surviving cells from the defected or injured tissue; these cells serving as template cells on the scaffold matrix;
(iv) treating the stem cell concentrate of step (ii) ex vivo without having expanded them, with EPO or hGH or other factors that stimulate stem cells and accelerates remodeling of tissue cells for 10-30 minutes in a bioreactor or a laminar airflow cabinet located in the operation room under sterile conditions;
(v) treating the template cells of step (iii) ex vivo, with at least one factor selected from the group consisting of EPO, hGH, GM-CSF, G-CSF, and TGFβ for 10-30 minutes in a bioreactor or a laminar airflow cabinet located in the operation room under sterile conditions;
(vi) coating or injecting the scaffold ex vivo with the pretreated cells of steps (iv) and (v) for 10-30 minutes in a bioreactor or a laminar airflow cabinet located in the operation room under sterile conditions;
(vii) prearranging the patient for implantation while carrying out steps (iv) to (vi)
(viii) implanting the partially or completely coated scaffold of step (v) into the tissue defect or wound; and optionally
(ix) applying by topical administration a gel-like or glue-like composition or formulation onto the implanted scaffold and onto the tissue in the environment of the implant, wherein said composition or formulation comprises the cells of steps (ii) and (iii) and one or more of the factors of step (v).

A method as specifies above, wherein a composition or formulation comprising at least one factor selected from the group consisting of EPO, hGH, GM-CSF, G-CSF, and TGFβ was applied to the patient in an pharmacologically effective amount by systemic administration before starting the operation with step (i).

DETAILED DESCRIPTION OF THE INVENTION

(A) Definitions

The term "supporting factors" as used in this invention is comprised of a group of factors consisting of: "cell factors", "boosting factors", "commitment factors", "recruitment factors" and "permissive factors".

The term "cell factors" is related in particular not really to factors like growth factors and the like, but to specific cells, which elicit or have retained their capability to differentiate to tissue cells of specific phenotype and with specific biological function. The very preferred cell factors or cells according to the invention are all kind of stem cells such as embryonic stem cells or adult stem cells such as mesenchymal stem cells, for example, obtained from peripheral blood or bone marrow cells. Stem cells are present in all tissues being CD90 positive. These cells can be isolated by collagenase digestion from skin, liver and heart tissue amongst most other tissues. The cells do not only express CD90 but also other markers found typically in bone marrow cells.

The cells however do not only express the receptor for erythropoietin but also for its subunit beta-cR. Beta-cR is a target for EPO and it's remodeling activity of extraclleluar matrix in CD 90+ Cells. This shows that a co-expression of the beta-cR exists in tissues such as skin, spleen and kidney in parallel to the expression of the growth hormone receptor GHR. The expression of the beta-cR is indeed found in all tissues together with the GHR. Thus, all cells expressing the beta-cR are suitable "cell factors" according to the invention. The expression of the beta-cR is indeed found in all tissues together with the GHR. In FIG. 1 the expression of the beta-cR and growth hormone is shown in skin, spleen and kidney in an exemplary way as it is not limited to these tissues but generically coexpressed The term "smart graft" or "smart scaffold" means a highly specific tissue template that senses a wound environment into which it is implanted and reacts accordingly using this environment to achieve it's own remodelling to a specific target tissue by stem cell activation leading to a high quality scar free tissue specific result The term "boosting factors" as used in this invention describes respective preferably natural biological molecules that stimulate the above-mentioned receptors on CD90 positive cells, preferably stem cells. The purpose of these "boosting factors" is to enhance remodeling, to reduce inflammation and to activate stem cells to propagate and to protect against ischemia and other tissue damages. The group of factors includes besides erythropoietin thrombopoietin and HGH. This includes also derivatives and peptide sequences of erythropoietin that eg. stimulate the beta-CR subunit of the erythropoietin receptor, the receptor of TPO or the growth hormone receptor. Inflammatory cytokines exhibit a stimulatory effect on mesenchymal stem cells, when co-stimulated in the presence of erythropoietin In this situation CD90 positive stem cells (fibroblast like progenitors) could be triggered to be activated in vitro. Erythropoietin alone has no triggering effect on fully differentiated cells, which means it does not act as a growth factor would typically do, but has according to the invention a sensing role linking a trauma dependent stem cell activation to a regenerative growth response. This means, that a site specific activation process is provided by the local wound environment at the time of transplantation. The human body apparently is able to react to localized trauma by triggering a site specific response that leads to repair. The knowledge for site specific repair must be linked to the combined mode of activity of trauma cytokines and boosting factors. According to the present invention the "boosting factors" are ideally co-transplanted by either pre-incubating the cells during the preparatory phases or by integrating them (full thickness, micro-patterning) and or positioning them together with other supporting factors into the scaffold for transplantation. Thereby the scaffold becomes a material that can release signaling factors to the cells at the time of inoculation and ideally during the total or partial period of duration of its existence. This represents a protracted release mechanism. Examples for suitable boosting factors according to the invention are: EPO, TPO and human growth hormone (HGH).

The term "recruitment factor" means according to the invention, preferably but not limited thereto, a natural biological molecule that is able to increase the number of stem cells both in situ and in the peripheral circulation. Recruitment factors can be added in addition or alternatively to in situ loading of the graft with intraoperatively prepared stem cells.

The term "commitment factor" means according to the invention, preferably but not limited thereto, a natural biological molecule that is able to control and direct differentiation, preferably in situ rather than in vitro, of stem cells, progenitor cells thereof, and cells which are not fully differentiated. Examples for such a factor according to the invention are: some hormones, vitamins such as vitamin C, A, and E, TGFβ and VEGF.

The term "permissive factor" means according to the invention, preferably but not limited thereto, a natural biological molecule that is usually present or generated during inflammation of a wound, such as the typical trauma cytokines. In vitro these trauma molecules are usually not present and can be additionally added to the cells obtained and treated by the teaching of this invention. Another permissive factor is constituted by ischemia itself. These molecules and conditions indicate site specificity and need and contribute permissive factors for stem cell activation in the simultaneous presence of the supportive and commitment factors. This indicates why this process is so rapid to induce remodelling of the graft and represents a powerful tool box to achieve graft remodelling if applied simultaneously according to the teaching of the present invention. In case of chronic or degenerative conditions that lack inflammatory conditions or in the absence of any trauma or injury there are at least two ways according to the invention that are used to achieve a full panel of stem cell stimulation: A) coadministration of trauma cytokines such IL-1, TNFalpha, IL-6 in very low and preferably topically restricted ways. This includes e.g. coating or intregration in the scaffolds used. B) In minor cases (regarding the defect size to be regenerated) mechanical stimulation with e.g. a needle, superficial rubbing for reddening, UV exposure, laser exposure, and knife cutting results in a endogenous release of such permissive factors. This process must therefore be done simultaneously to the application of the other factors and with and without the stem cells.

The possible problem of the availability of the factors according to the invention can be circumvented by using freshly harvested autologous tissue cells obtained from the tissue to be generated or healed of the same patient. These tissue cells can be applied in form of mingled tissue pieces, which can be added to the stem cell concentrate or composition provided for implantation, coating the scaffold or systemic administration solely or in addition implantation.

Each and all of these factors and their use according to the invention may overcome the problem of limitation of a "blind" transplantation into a tissue environment or a synthetic or biological/natural scaffold.

The term "intraoperative" or "intraoperative process" or "intraoperative implant engineering process" according to the invention means a process, wherein preparation of the implant/scaffold ex-vivo and surgery of the human or animal body at the site where tissue is defected, traumatized or injured is accomplished in principle in parallel, including biopsy of respective cells for loading the scaffold ex vivo in timely conjunction. That means that ex vivo activities regarding stem cell or other cell preparation and pretreatment thereof including incubation of the supporting matrices (scaffolds) are started shortly before or simultaneously before surgery of the diseased tissue, organ, joint etc. and ends after having implanted the scaffold loaded with cells and factors as describes above at the latest. The term also includes the application of the so-obtained or so-treated cells and factors in form of a suitable composition or preparation, preferably as a gel or glue formulation, for treating the implanted scaffold and the tissue environment around the implant and the defected or injured tissue surrounding the freshly implanted scaffold.

(B) Description of Details and Specific Embodiments

The invention is characterized by the fact that the cells are cotransplanted with a diversity of different factors as specified above. These factors are acting according to the teaching of the invention in situ and control and induce differentiation and growth in situ too.

According to the invention the factors are administered preferably topically in combination with a scaffold ex vivo and/or in vivo and simultaneously with and without the presence of exogenously administered (stem) cells. It is also possible to apply only some of the factors mentioned above. Furthermore, in a preferred embodiment of the invention the factors, as well as the respective cells (stem cells, patient's tissue cells) can be administered solely or together with a preferably pretreated scaffold/implant by systemic administration applied to the patient to be treated in good time (1-5 days) before surgery and starting the process according to the invention.

The invention is further characterized that, by applying the factors according to the invention, it fully avoids to perform an in-vitro culture that includes any expansion of cells, including stem cells. An advantage of this embodiment is that the time frame needed for the cell preparatory phase can be shortened to a matter of minutes thus eliminating the disadvantages of cell expansion and cell differentiation in vitro. If there is no cell replication in vitro risks are significantly reduced and/or abolished. On the other hand this embodiment allows control of differentiation in situ at the trauma (implant site) in combination with a boosting factor exposure, like EPO.

The single factors as specified by the invention interplay with each other and the cells, preferably the stem cells in situ at the trauma site:

The factors are used to coincubate the progenitor cells at the time of transplantation, or can be used to coat directly the scaffold. A "commitment factor" as specified by the invention can thus be applied also in a patterned way to a scaffold. In a collagen or hyaluronic/or chitosan sponge TGF beta 1, 2, or 3 is used to trigger mesenchymal stem cell differentiation at the implant site. Thus the interaction of boosting and commitment mechanisms is facilitate leading to significantly faster and qualitatively higher form of tissue regeneration. The difference is explained by the fact that conventionally differentiated cells in case of cartilage cells derived from MSC (mesenchymal stem cells) need 2-4 weeks to be prepared before implantation. Still thereafter cells loose not necessarily maintain their differentiation in vivo following implantation. Is is well known in the art, that normally cartilage generated in vitro or in vivo dedifferentiates to fibrotic tissue within a few months. According to the invention high quality hyaline cartilage results that is maintained in animals for at least 1 year (equivalent to 5-7 years in man). The technology according to the invention results in a faster preparatory phase (eliminating completely week long cultures), it is better from a quality point of view (fibrosis/scar free) and it is more economical from a production point of view. The cellular production complies with GMP (good manufacturing product condition).

In a tracheal scaffold, for example, the cartilage rings have a circumferential arrangement and a broadness of 3-4 mm. Here every very few millimeter another differentiation zone can be marked. Thus, a combination of factors according to the invention, for example commitment factors, can be used for patterning scaffolds. One commitment factor is e.g. vitamin C that can be patterned in areas in between cartilage rings to support matrix synthesis and development. Another example for a commitment factor is IL-15 that supports bronchial epithelial development and can be positioned in the lumen of the tracheal scaffold.

As outlined above boosting factors, such as EPO or GH are by definition cooperating with local trauma conditions and react towards them in a responsive way. As a matter of completeness, this is explained by the expression of trauma cytokines, which is known in the art, (J Trauma, 2008, vol. 65, n° 6, pp. 1374-1378,). There is a physiologic occurrence of these factors including trauma cytokines. IL-12 (p70), and IL-18 and Th2-type cytokines IL-4, IL-10, and IL-11 were determined using the enzyme-linked immunsorbant assay technique in patients and in healthy controls. IL-2 and interferony were seldom detectable. All other mediators were significantly increased matched to controls (p<0.05). All cytokines were elevated most prominent during weeks 1 and 2 posttrauma and declined thereafter. Other cytokines include IL-1, IL-6 and TNF alpha, and support the boosting effect of EPO/TPO and Growth hormone. The permissive factors allow CD90 cell generation in trauma areas upon EPO (boosting factor) stimulation scar free healing. This is relevant, for example, for cardiac ischemia, spinal cord injury, cartilage repair, tendon regeneration and all other tissues as it means "restitutio ad integrum" rather than defect (scar like healing).

An important function of the factors according to the invention, such as the boosting factors, is to increase the expression of stem cells (such as C90 positive cells) in the presence of trauma. In FIG. 2 it is shown that C90+ (Thy1) occur normally in the vascular trees. A and B show normal liver parenchyma in a rodent model. If the tissue is exposed to EPO (250 Units/kg bodyweight) C90+ cell expression is switched on everywhere in the parenchyma within 24-48 hours reaching peak heights of 1 in 5-10 cells being CD90+. It is also shown in FIG. 2 (C) that trauma alone as a pathophysiological condition is not any different from a non-trauma condition with respect to CD 90+, i.e. the parenchyma is free of CD90+ cells.

B also shows that this effect is not dependent upon EPO, since in the absence of trauma CD90+ cells are not stimulated to appear. The stimulatory result is rather dependent on a sensory and responsive function of EPO to stimulate the expression of CD 90+ cells in case of trauma (D). This sensory function is shown in FIG. 2. Only in the conditions accompanied with trauma EPO use leads to the expression of the CD90+ cells. These cells assume a pivotal role in assisting scar free or fibrosis free healing in all injury situations (FIG. 2).

The technology according to the invention carries the possibility to perform a simultaneous recruitment of stem cells by coadministering molecules such as GM-CSF or GSF to increase the availablitiy of MSC from the bone marrow at the sites of need. It is important that these cell recruting activities are done in a timwise identical or overlapping conditions. The topical integration again provides a slow release component and the possibility to use very low concentrations of less than 200 µg/m² body surface.

Also in a situation when exogenously obtained stem cells are applied e.g. harvesting from bone marrow or any other site in the body the coadministration of such recruitment factors secures a maintenance of the regenerative signalling not occurring physiologically any more in severely injury conditions.

According to the invention to complete the network of simultaneous interplay and onset of regeneration, the "recruitment factors" are preferably added to increase the number of stem cells both in the peripheral circulation and to exert a topical recruitment of stem cells. The novelty with respect to the invention is its simultaneous timing and role in regeneration in combination with e.g. a scaffold itself (cell free at time of implantation) and alternatively a scaffold inoculated with stem cells at the time of implantation. A third alternative is that no scaffold is used. This is especially advantageous in neuronal diseases including Multiple sclerosis, stroke, Alzheimer, psychiatric diseases and neurodegenerative disorders not responding to a an isolated stimulation of a single factor (e.g. EPO) in a complete and sustainable manner.

FIG. 3 shows a summary of the invention and interaction of contributing components to achieve the maximum healing response. To this purpose the supporting factors may be coated but preferably integrated into (inside) the scaffold materials. This allows that during the remodeling process of the transplanted scaffold a concomitant release to stimulate the advancing cells during the remodeling process is achieved. This means, that a site specific activation process is provided by the local wound environment at the time of transplantation. The human body apparently is able to react to localized trauma by triggering a site specific response that leads to repair. The knowledge for site specific repair must be linked to the combined mode of activity of trauma cytokines and boosting factors.

The process starts by procurement of approximately 100 to 200 ml of peripheral blood (adults, 10-50 ml in children) and centrifugation to obtain the so called buffy coat, containing the CD45+ progenitor cells. Alternatively stem cells can be obtained by aspiration of bone marrow. These stem cells are prepared in a manner to prevent clotting of the aspirate by addition of Heparin or a chelating agents. The cell aspirate may be concentrated or used directly after induction of polymerization and applied to the graft as bio-polymer coating. In this case the blood or plasma components of the stem cell aspirate are induced to clot by addition of Thrombin or Ca++. In addition a collagen based sponge, sponge fragments or collagen powder can be mixed into this preparation to enhance the cohesive and sticky strength of the polymerisation result. Simultaneously this gel like preparation needs to be applied to the surfaces of the scaffold material e.g. a tracheal matrix. In this case the stem cell gel is applied mostly on the external side of the implant. Before that stem cells were incubated with TGF beta3 and erythropoetin. These cells are applied in a circumferential and ring like preparation onto the scaffold. The luminal side and the peripheral site are also pretreated with EPO and TGF beta3 (trachea). The addition of the stem cells in this manner also contributes to achieving a simultaneous enhancement of vascularization of the graft by stem cell activation. The topical application of the diverse factors named, results in rather high topical concentration but very low systemic availability. A systemic application may be followed in a conventional manner.

According to this invention any graft scaffold (e.g. an acellularized or native heart valve or acellular or native trachea) can be initiated as a template to remodel fast. The whole process only require minutes or just 30-45 minutes to prepare. In this sense the material to be remodeled becomes a material that provides the copy—information for the result without being a fully developed graft.

The main advantage of this approach is, that the need for stem cell expansion and predifferentiation before transplantation is abolished completely. In addition the best quality of the implant is achieved as measured by histology and function following remodelling. A further advantage is the site specific mode of action of the commitment factors, that avoid systemic side effects. According to this teaching it is the local presence of permissive factors that together with the exogenously administered boosting factors allow an extremely rapid graft preparation to be done.

Alternatively stem cells can be obtained by aspiration of bone marrow. These stem cells are prepared in a manner to prevent clotting of the aspirate by addition of Heparin or a chelating agents. The cell aspirate may be concentrated or used directly after induction of polymerization and applied to the graft as bio-polymer coating. In this case the blood or plasma components of the stem cell aspirate are induced to clot by addition of, for example, thrombin or Ca++. In addition a collagen based sponge, sponge fragments or collagen powder can be mixed into this preparation to enhance the cohesive and sticky strength of the polymerization result. Simultaneously, this gel like preparation needs to be applied to the surfaces of the scaffold material e.g. a tracheal matrix. In this case the stem cell gel is applied mostly on the external side of the implant. Before that stem cells were incubated with TGF beta3 and erythropoietin. These cells are applied in a circumferential and ring like preparation onto the scaffold. The luminal side and the peripheral site are also pretreated with EPO and TGF beta3 (trachea). The addition of the stem cells in this manner also contributes to achieving a simultaneous enhancement of vascularization of the graft by stem cell activation. The topical application of the diverse factors named, results in rather high topical contraction but very low systemic availability. A systemic application may be followed in a conventional manner.

According to this invention any graft scaffold (e.g. an acellularized or native heart valve or acellular or native trachea) can be initiated as a template to remodel fast.

The following exemplary but not limiting protocol was developed for scaffold remodeling:
1) preparation of the scaffold in a sterile manner
2) Integration of erythropoietin as a sterile powder into the scaffold thickness to achieve depot effects, injection 3) Incubation of mesenchymal stem cells that have been freshly harvested from bone marrow with EPO (250 IU/Kg body weight), time
4) Incubation of peripheral blood mononuclear cells that have been freshly harvested with EPO (250 IU/Kg body weight)
5) Blood derived PBMC inside, bone marrow outside preferably in mixture with local epithelium islands and tissue biopsy fragments from healthy tissue is recommended.
6) Incubation/coating of the scaffold with TGFβ, partyhroid hormone, insulin, dex (alternatively slow release formulation form nano-carriers such as hyaluronic acid)
7) Intraoperative inoculation of these cells in a sterile device for seeding (rotational or coating process).
8) Implantation following ca. 45 min.

FIG. 4 describes graphically the process flow of the method to achieve scar free healing and "restitutio ad integrum" in a patient. A major advantage of the technology is, that if forms the basis for the highest standard achievable to date if compared to the state of the art with respect to sterility, safety, reproducibility, economics, quality of the result and mass applicability. Following procurement of the stem cells under sterile conditions and their preparation all processes are immediately continued directly in parallel to ongoing medical or operative treatment in a patient-side or intraoperative processing. The major advantage comes from the time sequence of events, that avoids extramural processing, leaving the operative theatre, leaving the hospital, cell expansion, complex transport logistics (car, train, airplane and other courier services) and cellular transformation and oncogene activation, cell selections or cloning due to artificial in vitro culture conditions and unwanted manipulations and dedifferentiation of the cells as well as infectious risks.

The handling can immediately done in a clean room situation that benefits from not having to leave the immediate treatment area, which is in all operative situations the operating room being the primary clean room. This offers a number of safety and GMP advantages already. The processing of cells is then done in <<class A>> environment equipped with bioreactors, sterile vessels, sterile ice, holding racks for tubes, sterile cloth covers and presterilized tools. The stem cell concentrate is transferred from the harvesting vessel to inoculate the scaffold that has been prepared in a sterile packaging (e.g. a heart valve scaffold, a collagen sponge). The bioreactors may contain the scaffold already and the respective lyophilisates of the boosting, commitment or recruiting molecules. In a first device the stem cells being provided in a blood or bone marrow or other form of (fat stem cells especially) concentrate are exposed to these factors and stored on ice. In the meantime the scaffold is prepared by injection of the boosting, commitment and/or recruitment factors under the laminar air flow. The bioreactor or device holding the scaffold is placed on a weight measuring instrument to document the weight gains. This instrument is recorded on line using specific software. This software also records the weight gains when in the following step the stem cell concentrate is applied to the scaffold. Inside the hood temperature and air particle concentrations are recorded on line and visualized on a screen next to the hood. The software also documents the time from start of air filtration to the start of the protocol to ensure sterility. As a minimum time is required for clearing the filters the device is switched on appropriately. The person handling the cell processing is using an e.g. foot controllable instrument linked to the server (PC, or avoiding contamination to the hands) to confirm completion of the specific steps to be allowed to advance to the next steps of processing the cells and scaffold. The software thus has a controlling and releasing function besides documentation of the process. This turns the device according to FIG. 10 into an autonomous self-controlled GMP production unit for stem cell processing. The whole process is video recorded from an integrated camera that also feeds the data into the software. This is important for documentation that the processes have been obeyed according to the GMP protocols. Termination of the preparatory process and confirmation by the specific worker doing it permits release of the bioreactor and transport to the operating table. Before transport the bioreactor/device is closed or covered to rule out inlet of contaminants from the air within the operating room (usually class B or C quality). In case a centrifuge is used for the stem cell preparation the centrifuge may be placed outside the production unit if a closed processing is possible. The centrifuge and its manipulative steps are equally recorded by the specific software. After removal of the implant the production unit is cleaned and decontaminated to be prepared for the next patient. Both is equally recorded by the software and confirmed by the worker doing it. All the information collected is transferred either online wherever possible to a centralized registry. In this registry the patient data including diagnosis, disease states and post-treatment course is fed by the doctors/treatment personnel. This assures a complete quality control and accessibility to third party independent quality controls. This approach of intraoperative processing, technology provision and software steering and control permits in association with a third party quality control the world's highest standard of stem cell implant production at the same time while lowering manufacturing cost by a factor of 10-100 over conventional processing. The combination of these process flow advantages represent the key to mass production and mass availability of individualized implants/personalized stem cell based implants. The scientific invention therefore opens the way for a critical industrialization technology that fully complements the scientific, technological and healing advantages of the process and method of this invention.

FIG. 11 summarizes the flow integration for the quality control components according to the invention. The quality control includes the stem cell harvest, stem cell preparation, inoculation steps inside the mobile production unit. All steps are recorded on-line in real-time and independent from manipulative intervention of the worker (doing the stem cell handling) by automatic collection of data. Parameter control precedes the release of the implant. The bioreactor/delivery device is sealed/closed before transferal to the operator. The opening is again documented. The process ends by the documentation of patient conditions.

The device of FIG. 10 is defined as a production unit, that contains the following components in a modular way to function properly according to the invention: A software master controlling all operations and thus forming an operative unit that has sensory, measurement and control functions as well as an overall documentation purpose. The instrumental components of the complete assembly include a laminar air flow conditions of class A, a bioreactor or cell culture device, a video camera, a temperature sensing instrument. While variability exists with respect to the different inoculation of cell culture processing instruments (bioreactors) or petri-dishes the basic advantage of the production unit is its flexibility in this modular design linked to an equally flexible control brain component that lets it function as an autonomous production unit in any operative or treatment environment to achieve custom mass production of individual implants ad hoc in the best quality possible.

In addition and according to the invention an apparatus such as a rotational bioreactor as described previously is used to perform the inoculation procedures in a sterile environment directly inside the operating theatre. The major advantage of the invention comes evident at best, if such apparatuses are used inside a laminar air flow system that provides a class A clean room inoculation cabinet. Bioreactors mounted inside these systems could be run as mobile units inside the operating room just for one patient at a time. In this sense a fully closed production environment is created according to the invention consisting of a mobile laminar air flow system or isolator that contains inside the processing unit, that is brought in contact with the patients cell or blood. These internal devices (bioreactors) are ideally single use (one-way) systems that are positioned on mounting racks that are reusable. It is this combination of a single use device, mobility, class A inoculation and processing and reduced size that allows to use the whole system as a production cabinet intraoperatively for stem cell processing according to the method described above.

According to the invention, EPO is added for example to the stem cell concentrate as solution or as a lyophilisate, preferably as a lyophilisate at a concentration of 150-300, preferably 200-250 Units/kg bodyweight. For topical administration the doses may be higher.

The stem cell concentrate is adjusted in volume to the type of tissue to be regenerated. It is 0.5-1 ml in a topical application, 2-3 ml for a transcutaneous positioning, for example on top of an infracted area in the heart. It can be 10-30 ml for bone regeneration in the mandibula.

This flexibility is achieved by spinning down the complete bone marrow, adipose tissue, blood volume obtained at a speed that allows sedimentation of all cells contained in the original volume. Also a plasma separation (cell free) results. While the very bottom contains a pile up of cells, integration of more volume is always possible with this technique having thus access to an enriched bone marrow concentrate with platelets and red blood cells. Previously, these other components were intended to be discarded. An advantage of this approach is to benefit from the interaction potential of those cells that delivers superior results over the isolated use of e.g. immunologically isolated CD133+ cells, which makes the difference between scar free over scar-like healing.

The topical applicability of G-CSF or GM-CSF in combination with stem cells allows to use a very low concentration if compared to standard systemic applications. In a standard approach 200 µg are coated onto e.g. the scaffold to be remodeled at 10-20 injection sites. EPO can be co-administered simultaneously or shortly before or thereafter by systemic administration. The injection used the stem cell concentrate. For a period of 1-2 weeks thereafter the compounds are injected, e.g. s.c. in the same quantities.

For cartilage regeneration TGFβ is added to these injections into a scaffold of 100-500 ng for a 10 cm² patch.

Vitamin C is added especially for neuronal sprouting into a scaffold at 500 µg. Vitamin E is added especially for neuronal differentiation with 30 000 IU.

Viscous gel or hydrogels comprising biological factors or tissue cells are well known in the art. According to the invention preferably polymeric compositions such as polymeric cellulose gels based on, for example, carboxymethyl cellulose can be used to manufacture the respective formulations.

DESCRIPTION OF THE FIGURES

FIGS. 5a (top) and b (bottom): This example shows a synthetic graft surface following inoculation with progenitor (stem cells) harvested from the iliac crest and peripheral blood. The cells were mixed into autologous plasma (3 ml). This plasma was brought to polymerization by addition of Thrombin (0.1 units/ml) and applied to the outside of the graft. An advantage of the process according the invention is, that a clot is formed that permits initiating processes like in normal wound healing. Clotting kinetics, clot structure and clot fibrinolysis create a microfiche that if combined with boosting factors, commitment factors and recruitment factors according to the invention is ideal to star a scar free healing process. The graft is created then inside the recipient body within 1-2 weeks.

Figure 1:
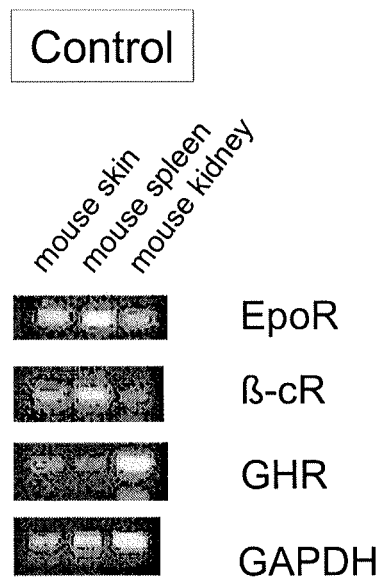
FIG. 1: Expression of EpoR, beta-cR and growth hormone receptor in parallel in tissues and stem cells.
Figure 2:
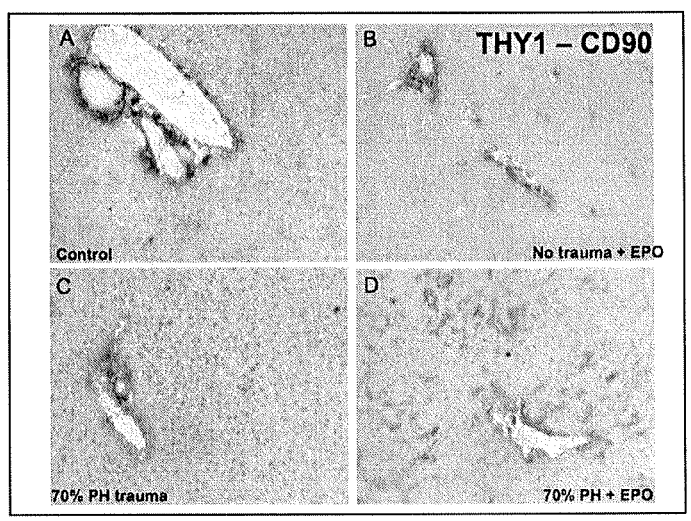
FIG. 2: This example shows use of the invention to induce the expression of stem cells in the liver parenchyma: A and B represent the non-trauma groups, C and D the trauma groups. The addition of rhEPO generates the expression of CD 90+ cells in the liver parenchyma only in the trauma groups.

On the inside (b) the cells were dripped on the luminal surface using a syringe. In b the continuation in vitro using is shown at 14 days. The culture continued under standard conditions.

FIG. 5c (top) and d (bottom): this example shows a graft prepared according to the invention. It is cut open longitudinally and exhibits a very nice and shiny (non-thrombogenic) lumen. In this large animal model at 4 weeks the controls always (d) clotted. This would be a compete clinical failure.

The fluorescent cells indicate almost 100% viability both luminally and on the outside. The bone marrow/plasma gel represents a 3D nourishing microenvironment that forms a 3D growth zone even if unfavorable conditions would exist initially on the graft materials (see later allogeneic or xenogeneic heart valves that are coated in the same manner).

FIG. 5e (top) and f (bottom): This figures reiterate the results from a graft implanted at 4 weeks and prepared according to the invention, looking at the histology. In 5e the graft polymer core is shown with neo-tissue generated towards the luminal and peripheral side. The non seeded graft exhibits a thrombus towards the lumen. In FIG. 5f the neo-tissue generated is shown surrounding the synthetic core (non-degradable) fiber material.

FIGS. 5g (top) and h (bottom): FIG. 5g shows the CD31 (endothelial marker) staining of the luminal side of a graft prepared following the invention. A neo-formation of a vascular endothelium has occurred that prevents the thrombus formation. 5h shows a biological scaffold demonstrating that reendothelialization from progenitors can occur also using a biological matrix (xenograft)

FIG. 6: A heart valve is prepared following a decellularization. It is shown that according to the invention a physiology indistinguishable from a normal valve is achieved. Valves are implanted into the aortic position. No failure from the high pressure area has resulted.

FIGS. 7a and b: FIG. 7a (top) shows the implantation after a bioreactor culture with stem cells prepared in a plasma gel. The culture in vitro was done for 1 week. This X-ray results correspond to the group D of 7b (bottom) and show a good progression of bone strengthening over the observation periods of 2, 4 and 6 weeks. On the bottom side (FIG. 7b) picture A is the control defect (critical size defects were established in a pig model), picture B: inoculating tri-calciumphosphate with blood only results in a weak bone trabecle formation, picture C: intraoperative mixture (as done in state of the art, not according to the invention) of the bone replacement material with bone marrow from the recipient, showing a partial progression of healing only. Picture D shows in contrast in this experiment the best result of complete bone regeneration in a critical size model of a bone defect. This proves that the mere use of bone marrow to inoculate the materials is not sufficient to achieve the same progression of regeneration as a standard cell culture with a respective stem cell expansion and ostoblast differentiation would be able to achieve. This inferior quality of the state of art is a conventional form of intraoperative bone marrow use for bone support. As shown in the following figures the advantages of the process and technology according to the invention become clearly evident:

FIGS. 8a (top, according to state of the art, 6 and 16 weeks after implantation) and b (bottom, example using the invention, 6 weeks after implantation)

FIG. 8b shows the results of the bioreactor culture (7 day/1 week bioreactor culture) over the controls A: material (TCP+blood) over the intraoperative technology according to the invention combined with EPO. D is a control defect with no filling. All is shown at 6 weeks. It is evident that the intraoperative process (10) according to the invention is now as efficient as a week-long cell culture process. It is also evident from FIG. 8a that an intraoperative seeding that is being done in a state of the art manner by just adding bone marrow does not lead to an adequate bone formation (a large hole in the bone is still present at 16 weeks, 8a intraoperative standard technique). 8b shows thus over 8a clearly the advantage of a combined process according to the invention, since healing is completed at 6 weeks already in all groups. The standard state of art intraoperative technique of 8a leaves in contrast a large defect both at 6 but also at 16 weeks (8a).

In larger defects bone marrow cells prepared according to the invention however will be advantageous over mere blood use.

FIG. 9a, (top) b (bottom)

This figure shows a patient that has received a stem cell treatment according to the invention with a defect size that is 100 times larger than the critical size defect used in FIG. 8. The healing progress is rapid (b) and shows a long-term sustainability of the neo-bone with an excellent quality of trabecular bone formation. Normally such an implant would have collapsed (state of the art using stem cell cultures of bone) at 6-8 weeks or would not have remodeled to this type of quality bone at all. Normally the material used remains with little remodeling for many years or is replaced with fibrotic tissue. In the process according to the invention no cell expansion was needed, no scar or fibrosis has resulted and the bone is stable for years.

FIG. 9c: final result after 1.5 years showing good bone morphology, no collapse but sustainability of the result.

Figure 10:
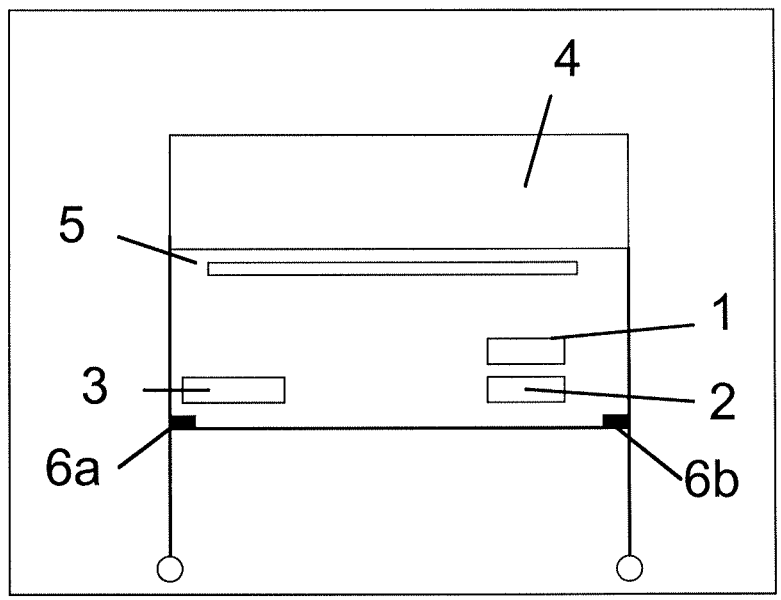

FIG. 10 shows an ideally mobile unit consisting of a one way bioreactor (a closable device) (1) mounted on a docking station or rack (as described previously), a centrifuge (3, may be outside alternatively) and a sterilization device such as UV light. 4 represents the sterile air filtration systems. It is a speciality of this combined device that it represents a miniaturized laboratory inside the operating room. This device can be used to perform cell culture processes that used to take 2-3 weeks in less than 1 hour according to the method of the invention. It is an important feature, that 1 symbolizing any bioreactor for tissue engineering, is ideally an one-way device. The system can move with a closed front window and maintain sterility completely by increasing air pressure inside over ambient air pressure to maintain sterile air flow inside (37° temperature controllable). To this purpose the air is removed outside by 2 uni-directional valves (6a and 6b) which are activated when the front window panel ist closed. In addition a monitoring system is included, which fully documents all bioreactor activities (position, temperature, rotations, pumping activity with respect to pressure, speed and volume, open and closed window). The system also measures air particle concentrations inside and causes alarms once the officially required class A thresholds are violated. All these technologies are known individually in the art, but if combined create a significantly increased value and applicability for a mobile stem cell engineered graft production inside of an operative theatre. The device is fully independent and comes with ist own electrical power supply (battery operated).

The system can be sterilized inside with gas or hydrogen peroxide. In addition the system has an antimicrobial surface that contains in one embodiment a silver coating achieved in plasma ionization.

Figure 11:
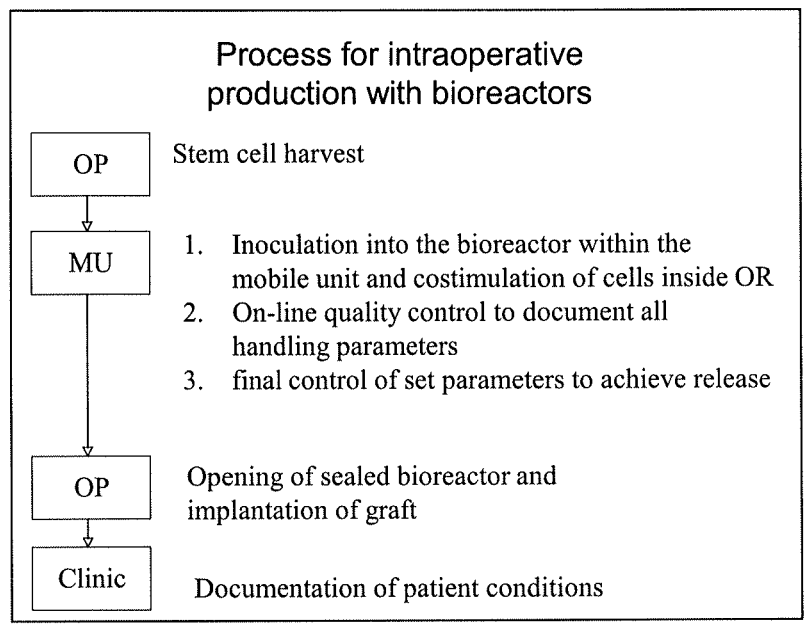

FIG. 11: Integration of quality control and documentation accompanying and completing the production requirements.

EXAMPLES

The following examples describe the invention in more detail. It is emphasized herewith that the choice of cells, factors, conditions, concentrations, methods, scaffolds, formulations etc. indicated in these examples are not limiting the invention and can be replaced, if not otherwise stated, by respective similar, adequate or equivalent, cells, factors, conditions, concentrations, methods, scaffolds, formulations etc., provided that a skilled worker would apply these modifications or alternatives without being inventive.

Example 1

24 hours before start of operation: erythropoetin sc (normal single dose according to manufacturer recommendation, 10.000 Units) and GM-CSF (normal single dose according to manufacturer recommendation 250 units/m2, 1 vial) to activate stem cell production in the bone marrow and to target autologous stem cells with EPO.

Start of anesthesia of the patient with tracheal defect to be repaired

Collection of 100 ml blood to obtain autologous plasma (anticoaglulate with low amount of Heparin)

Harvest for 30-60 ml of bone marrow aspirate from the patient from the iliac crest Placement of the blood/bone marrow on ice (4° C.) with sterile secondary packaging in heparinized tubes Preparation of operative situs and recovery of additional biopsies with a diameter of 1-2 mm if comparable target tissue is still available. Storage on ice in sterile container in sterile normal saline.

Transfer of bone marrow aspirate and tissue biopsies to laminar air flow located ideally directly inside or very close to the operating room Preparation of bone marrow and or blood aspirate or other stem cell source to achieve concentration and/or access of cells. Preparation of stem cells with all but not limited to all possible procedures known in the art including density gradient preparation, immunological separation, concentration, filtration, matrix digestion or mincing and washing.

Preparation of injection solutions by aliquoting stem cell concentrates or alternatively plasma and use as solvent for the boosting, commitment and/or recruitment factors.

Interim incubation of mesenchymal stem cells that had been freshly harvested from bone marrow with EPO/TGFbeta3 mixture (500 µl)-storage on sterile ice/room temperature (depending upon interval available and progress of parallel operation) and conditioning with those factors in vitro.

Injection of specific solutions in regularly distributed different sites into the scaffold for in situ delayed release after implantation and stem cell patterning trough later site specific commitment induction if cells encounter those factors at exactly those predetermined positions.

Injections of stem cell, with or without tissue mincing results into appropriate positions (e.g. in the lumen of tubular implants (e.g. valves, vessels, ducts) and intraluminal injection slightly underneath the superficial surface for cell island formation.

Transfer to the operative site and implantation

Coating of the stem cell mixture to the wall with autologous plasma or fibrin glue intraoperatively to allow gentle positioning and to avoid removal during implant handling. Implantation following 45 min Postoperative treatment of patient with boosting and/or recruitment factor until end of simulated wound healing phase (often 2 weeks, longer if necessary e.g. in spinal injury).

Example 2

Cardiovascular Engineering

In an experimental design six allogeneic and 4 xenogeneic valves were harvested in a sheep model of aortic valve replacement. 2 of the valves underwent an decellularizaton process using a detergent (chenodesocycholic acid) as known in the art. These valve were then stored at 4° and brought to the operative theatre in sterile condition. The valves were injected with Erythropoetin (5.000 units) and G-CSF (Leukine, Sargramostim) and Growth hormone luminally with a very small syringe diameter (0.5 mm) to reduce damage. Simulataneously bone marrow was harvested with a total volume of 30 ml. The bone marrow was spun down at 1500×g for 7 minutes. The centrifugation was done with heparinized blood. 1 cc of the remaining pellet was injected underneath the superficial matrix of the luminal side resulting in a patchy distribution of the stem cells. This served the purpose of protecting the cells from detachment after introduction into the blood stream. Following implantation the valves were coated with 5 ml of bone marrow concentrate that was prepared.

Example 3

Synthetic Graft Experimental Procedure

In this case a synthetic graft is used. Such grafts may be PTFE, polyester grafts, combined polyester with silicone grafts, collagen tubes, collagen—elastin grafts, biological grafts with or without decellularization. An induction of the polymerization process of the stem cell coating is achieved by adding a polymerization agent such as Thrombin (0.1 units/ml) or Ca++ antagonizing the clotting preventing agents used during the bone marrow or blood collection. The clotting kinetics lead as to a triggering effect for the subsequent healing process, clot structure and clot fibrinolysis create a microniche that if combined with boosting factors, commitment factors and recruitment factors according to the invention is ideal to provide a scar free healing process. Cells do not grow into holes or empty spaces. The gel obtained from the clotting process is preferably an artificially shaped polymer to achieve a specific geometry. The entrapment of cells is advantageous for establishing communication pathways between stem cells, platelets, fibers, red blood cells, white blood cells and all the entrapped stem cells including CD90, CD133, CD106, and CD45.

Figure 3:
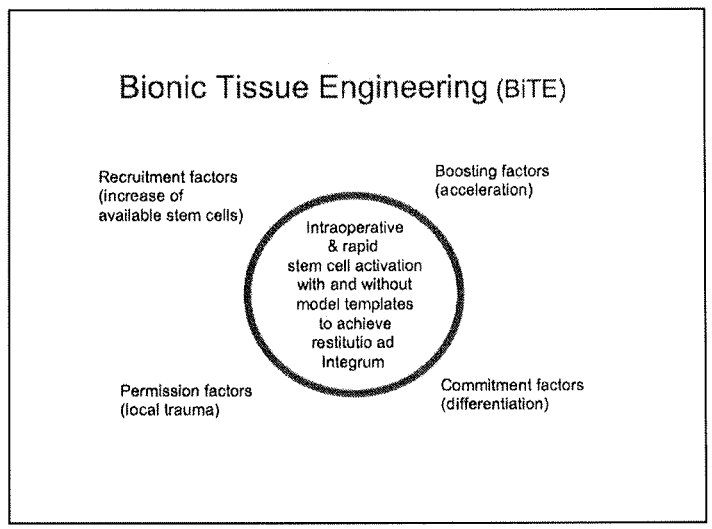
FIG. 3: This summarizes the interplay of the use of recruitment, boosting and commitment factors in the presence of a permissive situation (e.g. trauma). The stem cell preparatory process is accordingly adjusted and can thus be extremely fast requiring only minutes and is done intraoperatively. A template for remodeling is used depending upon size of the defect to be repaired.
Figure 4:
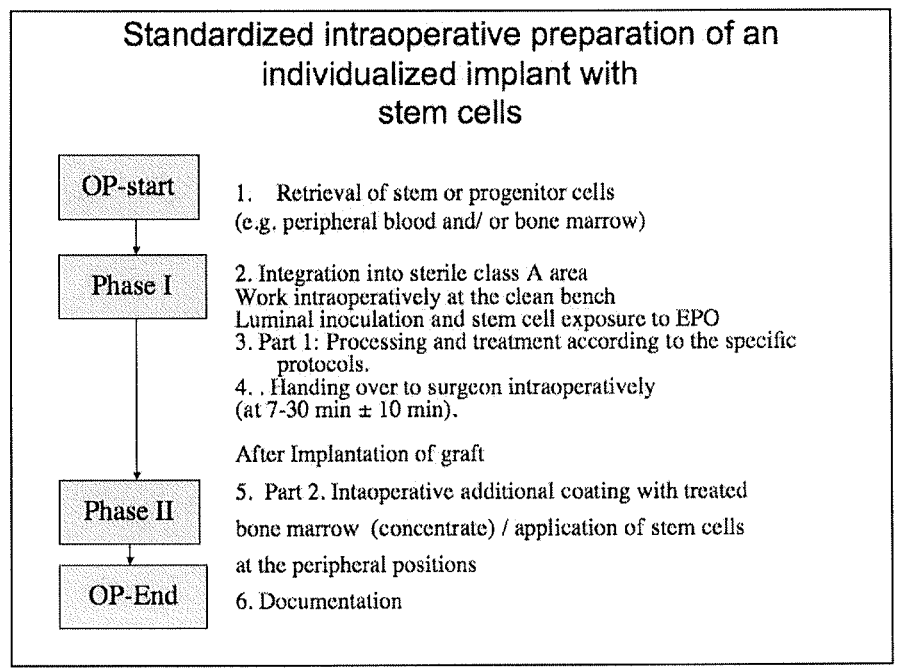
FIG. 4: This example shows a process flow linking the invention to an intraoperative sequence of events being divided in II phases. Phase I is an in vitro phase of cell preparation and stimulation. Phase II includes a stem cell application onto a graft following in situ positioning. E.g, a heart valve can be coated from the peripheral side, reducing risks of manipulative stess and detachment of the cells at the time of implantation.

The graft is created then inside the recipient body within 1-2 weeks. The slow release mechanisms lead to a controlled interaction of the graft coating with the cells starting the remodeling process from within. The process continues until cytokine stimulation derived from the wound area and the entrapped inflammatory cells is finished in parallel (simultaneously) to the healing results. It was found that IL-6, IL-1 and TNF are important trauma cytokines activating the stem cells (permissive factors). The polymerization process and the entrapment of the immunocompetent cells is supportive for the completion of the interaction cascade (according to FIG. 3 of the invention). Even on heterogenous of synthetic surfaces the neo-graft is formed with a fully biological luminal and peripheral side. The differentiated cells include fibroblasts, smooth muscle cells, endothelial cells (CD31+). The technology provides a significantly better potential of applicability as the thrombogenicity is reduced greatly. A hyperplasia has not occurred. An important application therefore is the treatment of endoluminal (cardio)vascular stents, which mostly fail due to hyperplasia especially end zones. A neoformation of a vascular endothelium occurs that prevents the thrombus formation. The scaffold may be decellularized with a trypsin based approach or using a detergent (e.g. chenodesoxycholic acid).

The following protocol can be used:

Intraoperative process for synthetic implant individualization using a polyester, collagen, chitosan, polyester+silicone coated graft, or e.g. but not limited to a PTFE graft 24 hours before start of operation: erythropoietin sc (normal single dose according to manufacturer recommendation, 10.000 Units) and GM-CSF (normal single dose according to manufacturer recommendation, 1 vial) to activate stem cell production in the bone marrow and to target autologous stem cells with EPO.

Start of anesthesia of the patient with graft defect to be repaired

Collection of 50 ml blood to obtain autologous plasma (anticoaglulate with low amount of Heparin)

Harvest for 30 ml of bone marrow aspirate from the patient from the iliac crest

Placement of these 30 ml on ice with sterile secondary packaging in heparinized tubes Preparation of tracheal situs and recovery of 5 bronchial epithelial biopsies with a diameter of 1-2 mm and storage on ice in sterile container in sterile normal saline Transfer of bone marrow aspirate and epithelial biopsies to laminar air flow cabinet for further processing.

Centrifugation of bone marrow aspirate for 7 min at 4° C. to achieve concentration of cells Separation of plasma from stem cell concentrate by transfer to a sterile tube on ice Preparation of erythropoietin solution using 1 ml of the plasma supernatant obtained from the centrifugation process (50.000 units, Neorecormone, Roche)

Addition of TGF beta 3 sterile to the EPO-plasma solution locally specific.

Incubation of mesenchymal stem cells that have been freshly harvested from bone marrow with EPO/TGF-beta3 mixture (500 µl)-storage on sterile ice Injection of EPO/TGF solution in 10 different sites of the tracheal scaffold for in situ delayed release after implantation.

Incubation of 1 ml stem cell, epithelial cell mixture in the lumen of the tracheal scaffold, and intraluminal injection for cell island formation Transfer to the operative site and implantation Coating of the stem cell mixture to the wall with autologous plasma or fibrin glue intraoperatively to allow gentle positioning and to avoid removal during implant handling. Implantation following 45 min Example 4

Valve Engineering

A major current tissue engineering limitations in the use of decelluarized tissues especially is the lack of stability and pressure resistance that complicates the use of such valves in a high pressure environment. Also the postulated growth in a pediatric environment was judged to be a dilatative response rather than true growth. These problems are resolved with the following protocol. Alternatively decellularized vessels or valves are equally quickly primed to perform fast remodeling in vivo. The process according to the invention can thus improve also decellularized matrices.

Valve Protocol: Intraoperative Process for Allogeneic Valvular Implant Individualization 24 hours before start of operation: erythropoietin sc (normal single dose according to manufacturer recommendation, 10.000 Units) and GM-CSF (normal single dose according to manufacturer recommendation, 1 vial) to activate stem cell production in the bone marrow and to target autologous stem cells with EPO.

Start of anesthesia of the patient with heart valve defect to be repaired

Collection of 200 ml blood to obtain autologous plasma (anticoaglulate with low amount of Heparin) and buffy coat.

Harvest for 10 ml of bone marrow aspirate from the patient from the iliac crest

Placement of these 10 ml on ice with sterile secondary packaging in heparinized tubes Preparation of valve situs and recovery of 5 valvular biopsies with a diameter of 1-2 mm and storage on ice in sterile container in sterile normal saline Transfer of bone marrow aspirate and epithelial biopsies to laminar air flow bench for further processing.

Centrifugation of bone marrow aspirate for 5 min at 4° C. to achieve concentration of cells Separation of plasma from stem cell concentrate by transfer to a sterile tube on sterile ice Preparation of erythropoietin solution using 1 ml of the plasma supernatant obtained from the centrifugation process (50.000 units, Neorecormone, Roche)

Addition of HGF and/or VEGF to the EPO-plasma solution

Incubation of mesenchymal stem cells that have been freshly harvested from bone marrow with EPO storage on sterile ice Injection of EPO/HGF solution in 10 different sites of the tracheal scaffold for in situ delayed release after implantation.

Incubation of 1 ml stem cell, endothelial/stem cell mixture in the lumen of the tracheal scaffold, and intraluminal injection for cell island formation, Use of unexpanded but freshly prepared cells Luminally buffy coat derived cells are seeded.

Transfer to the operative site and implantation

Coating of the stem cell mixture to the wall with autologous plasma or fibrin glue intraoperatively to allow gentle positioning and to avoid removal during implant handling. Implantation following 45 min Example 5

Airway Engineering

"Trachea Protocol": Intraoperative Process for Allogeneic Tracheal Implant Individualization"

24 hours before start of operation: erythropoietin sc (normal single dose according to manufacturer recommendation, 10.000 Units) and GM-CSF (normal single dose according to manufacturer recommendation, 1 vial) to activate stem cell production in the bone marrow and to target autologous stem cells with EPO.

Start of anesthesia of the patient with tracheal defect to be repaired

Collection of 50 ml blood to obtain autologous plasma (anticoaglulate with low amount of Heparin)

Harvest for 10 cee of bone marrow aspirate from the patient from the iliac crest Placement of these 10 cc on ice with sterile secondary packaging in heparinized tubes Preparation of treacheal situs and recovery of 5 bronchial epithelial biopsies with a diameter of 1-2 mm and storage on ice in sterile container in sterile normal saline Transfer of bone marrow aspirate and epithelial biopsies to laminar air flow laboratory for further processing (cryolab).

Centrifugation of bone marrow aspirate for 5 min at 4° C. to achieve concentration of cells Separation of plasma from stem cell concentrate by transfer to a sterile tube on sterile ice Preparation of erythropoietin solution using 1 ml of the plasma supernatant obtained from the centrifugation process (50 000 units, Neorecormone, Roche)

Addition of TGF beta 3 sterile to the EPO-plasma solution

Incubation of mesenchymal stem cells that have been freshly harvested from bone marrow with EPO/TGF-beta3 mixture (500 µl)-storage on sterile ice Injection of EPO/TGFβ solution in 10 different sites of the tracheal scaffold for in situ delayed release after implantation.

Incubation of 1 cc stem cell, epithelial cell mixture in the lumen of the tracheal scaffold, and intraluminal injection for cell island formation Transfer to the operative site and implantation Coating of the stem cell mixture to the wall with autologous plasma or fibrin glue intraoperatively to allow gentle positioning and to avoid removal during implant handling. Implantation following 45 min.

Example 6

Liver Engineering 24 hours before start of operation: erythropoetin sc (normal single dose according to manufacturer recommendation, 10.000 Units) and GM-CSF (normal single dose according to manufacturer recommendation, 1 vial) to activate stem cell production in the bone marrow and to target autologous stem cells with EPO.

Start of anesthesia of the patient with liver defect to be repaired. This includes typically patients with chronic cyrrhosis, acute on chronic liver failure, extensive liver resections including live organ donations and liver organ transplantation.

Collection of 200 ml blood to obtain platelet rich plasma (anticoaglulate with low amount of Heparin) and or PBMC, or a concentrate of all of it (combined for better effects and ease of preparation)

Harvest for 100 ml of bone marrow aspirate from the patient from the iliac crest Placement of these 100 ml on ice with sterile secondary packaging in heparinized tubes Simultaneous to an endoscopic operation and preparation of liver situs and recovery of 5 liver fragment biopsies with a diameter of 1-2 mm (obtained at a liver resection from an edge of the liver) and storage on 4° C. ice in sterile container in sterile normal saline Transfer of bone marrow aspirate and liver biopsies to laminar air flow bench for further processing.

Centrifugation of bone marrow aspirate for 5 min at 4° C. to achieve concentration of cells Separation of plasma from stem cell concentrate by transfer to a sterile tube on sterile ice Preparation of erythropoietin solution using 1 ml of the plasma supernatant obtained from the centrifugation process (10 000 units, Neorecormone, Roche)

Addition of HGF to the EPO-plasma solution

Incubation of mesenchymal stem cells that have been freshly harvested from bone marrow with EPO storage on sterile ice Injection of EPO/G-CSF/HGF solution in 10 different sites of a collagen sponge scaffold for in situ delayed release after implantation.

Incubation of a final 5 ml stem cell concentrate, liver tissue fragments/stem cell mixture onto the surface of the scaffold. Polymerization is achieved by adding thrombin.

Transfer to the operative site and implantation, attachment to the liver by gluing on top of a resected surface or on top of a cirrhotic liver. 10-20 small micropunctures on the surfaces to achieve blood access continuity with the sponge are done.

Coating of the stem cell mixture to the wall with autologous plasma or fibrin glue intraoperatively to allow gentle positioning and to avoid removal during implant handling. Implantation following 30 min Example 7

Skin Engineering

Protocol for Decubitus, Diabetic Ulcer, Ischemic Legs, Infected Wounds in any Area.

at start of operation: erythropoietin sc (normal single dose according to manufacturer recommendation, 10.000 Units) and GM-CSF (200 µg/m2 for a 70 kg patient/low dose) to activate stem cell production in the bone marrow and to target autologous stem cells with EPO. As the condition is often not comparable in severity GM-CSF or G-CSF may be omitted.

Start of anesthesia of the patient

Collection of 200 ml blood to obtain platelet rich plasma (anticoagulate with low amount of Heparin) and or PBMC, or a concentrate of all of it (combined for better effects and ease of preparation)

Collection of 30-60 ml of bone marrow aspirate from the patient from the iliac crest Placement of the collection results on ice with sterile secondary packaging in heparinized tubes Surgical debridement of infected wounds. Removal of necrotic tissue as normal.

Especially in burns or if granulation tissue is present in chronic wounds, a preparation of 10 skin biopsies with a diameter of 1-2 mm (obtained from healthy areas) serves the purpose to support the epithelialization. Specimens are stored on 4° C. ice in sterile container in sterile normal saline or autologous plasma Transfer of bone marrow aspirate and skin biopsies to laminar air flow bench for further processing.

Centrifugation of bone marrow aspirate at 4° C. to achieve concentration of cells Separation of plasma from stem cell concentrate by transfer to a sterile tube on sterile ice Preparation of erythropoietin solution using 1 ml of the plasma supernatant obtained from the centrifugation process (10 000 units, Neorecormone, Roche)

Addition of to the EPO-plasma solution

Incubation of mesenchymal stem cells that have been freshly harvested from bone marrow with EPO storage on sterile ice Injection of EPO/G-CSF solution in 10 different sites of a collagen sponge scaffold for in situ delayed release after implantation. Alternatively mixture with the stem cell concentrate and induction of polymerization.

Incubation of a final 5 ml stem cell concentrate, skin tissue fragments/stem cell mixture onto the surface of the scaffold. Polymerization is achieved by adding thrombin. If no scaffold is available the bone-marrow concentrate is brought to polymerization of a plastic surface (e.g. Petri dish, bioreactor). This forms a gel like a membrane, that can be transferred after gelling to cover the wound.

Transfer to the operative site and implantation, positioning to the wound (Transplantation following 30 min)

Alternatively or in addition the cell/factor mix is injected into the wound edges (5 ml total at 10 different sites).

Cover with a collagen sponge and complete cover of the are with a transparent film Example 8

Cardiac Engineering

Protocol Cardiac Ischemia, Heart Attack, Cardiomyopathy. The Goal is to Position a Stem Cell Gel According to the Invention Underneath the Pericardial Sac Via a Transcutaneous Way at start of operation, or even when patient is available after diagnosis of acute cardiac attack. EPO 10000 Units and/ G-CSF is given as an acute medication at 250 Units/kg bodyweight, G-CSF at 250 µg/patient of 70 kg. In not so severe cases EPO alone is sufficient.

Collection of 200 ml blood to obtain platelet rich plasma (anticoaglulate with low amount of Heparin) and or PBMC, or a concentrate of all of it (combined for better effects and ease of preparation)

Collection of 30-60 ml of bone marrow aspirate from the patient from the iliac crest, in local anesthesia Placement of the collection results on ice with sterile secondary packaging in heparinized tubes Start of local anesthesia of the patient at the chest.

Positioning of a catheter through the chest under x-ray control to reach the pericardium and positioning of the opening underneath the pericardium on top of the infracted area.

Transfer of bone marrow aspirate to laminar air flow bench for further processing.

Centrifugation of bone marrow aspirate at 4° C. to achieve concentration of cells Preparation of erythropoietin, G-CSF solution using 1 ml stem cell concentrate obtained from the centrifugation process (10.000 units, Neorecormone, Roche), storage on sterile ice.

Addition of the highly conserved serum response factor (SRF) and myogenin may be done to support cardiac muscle differentiation.

Induction of polymerization and injection via the catheter on top of infracted area.

closure of pericardium time needed: 10-20 min

Example 9

Cornea Engineering

The repair of the cornea especially when no healthy controlateral eye with intact limbal stem cells is available is not possible. In a conventional approach stem cells would need to be expanded as well. Other eye applications include macula degeneration, blindness, optical neuritis, dry eye. A deeper injection may be chosen for macula degeneration. According to the invention a threefold rapid process can be done:
- A) direct stimulation during acute injury after washing with the boosting factor EPO applied as a lyophilisate mixed with artificial lacrimae
- B) preparation of a corneal biopsy from the controlateral eye, mincing to achieve very small specimens, or gentle digestion to obtain isolated cells and washing. Incubation of the cell specimens with EPO and positioning on top of the eye. Alternatively cells may be injected underneath or into the damaged cornea. The cornea may be removed surgically in some areas. In very severe cases GCSF is given sc together with EPO until wound healing has completed (1-2 weeks)
- C) if no corneal biopsy is available at all stem cells obtained from PBMC or bone marrow concentrate are added to artificial lacrimae or plasma and positioned together with EPO and/GCSF onto or into the damaged cornea.

Example 10

Breast Reconstruction or Breast Implant

The repair of the breast is achieved by series of injections with a stem cell gel according to the inventions to build up missing tissue after resections. It is also used to prepare the surface of a breast implant to avoid scar and fibrosis formation. As commitment factors sexual hormones are used to trigger the maturation of the stem cells into the breast tissue lineage. According to the invention a two-threefold rapid process can be done:
- A) direct stimulation of the implant the boosting factor EPO applied as a lyophilisate mixed stem cell concentrate
- B) Preparation of a breast biopsy from the controlateral breast, mincing to achieve very small specimens, or gentle digestion to obtain isolated cells and washing. Incubation of the cell specimens with EPO and injection with stem cell concentrate. Alternatively cells may be injected in repetitive procedures to achieve build up. GCSF is given sc together with EPO until wound healing has completed (1-2 weeks). Hormones used include estrogen, FSH (follicle stimulating hormone), growth hormone, progesterone and prolactine.

Example 11

Spinal Cord Regeneration or Peripheral Nerve Regeneration

The regeneration of neurons is achieved by positioning a stem cell gel either on top of the ischemic area after decompression or by replacement using a collagen guide as a tube. With this stem cell gel according to the inventions the regeneration of missing neuronal tissue is possible. It is also used to prepare the implant to avoid scar and fibrosis formation. As commitment factors nerve growth factor is used, in combination with vitamin C (or alone for sprouting) and Vitamin D (for neuronal differentiation) to trigger the maturation of the stem cells into the neuronal lineage.

According to the invention a twofold rapid process can be done:
- A) direct stimulation of the wounded nerve tissue using the boosting factor EPO applied as a lyophilisate mixed stem cell concentrate
- B) Injections of GCSF, EPO, Vitamin C and Vitamin D sc over a period of up to 4-6 weeks if no surgical access is possible
- C) Interposition as a stem cell gel with the above factors induction of polymerisation. To enhance stability of the gel a collagen powder is mixed into the polymerising bone marrow stem cell concentrate with the factors.

Example 12

Tendon, Ligament, Intervertebral Disc, Meniscus, Cartilage Regeneration

The regeneration such connective tissue is achieved by positioning a stem cell gel either on top of the injured area or by injection into the injured area. To obtain material for the commitment minced original tissue is obtained from the disrupted or damaged areas (often from trauma). In a degenerative situation wound cytokines are generated by artificial puncturing with a needle to support the stem cell gel/factor mix according the invention. In the case of an intervertebral disc TGF beta is applied in addition to support the reformation of the nucleus pulposes. If fragments are available they are mixed together into the stem cell gel.

With this stem cell gel according to the inventions the regeneration avoiding scar and fibrosis formation is possible. As commitment factor fibroblast growth factor can be added for acceleration to achieve rapid results.

According to the invention a threefold rapid process can be done:
direct stimulation of the wounded tissue using the boosting factor EPO applied as a lyophilisate mixed stem cell concentrate Injections of GCSF, EPO, over a period of up to 1-2 weeks if no surgical access is possible (especially as a preventive measure)

Injection of a stem cell gel with the above factors induction of polymerization. To enhance stability of the gel a collagen powder is mixed into the polymerizing bone marrow stem cell concentrate with the factors.

In the case of cartilage regeneration a scaffold/gel prepared of chitosan is used and inoculated with the stem cell/factor gel including TGF beta (20 ng) at the time of implantation. Fixing of the gel/is achieved by gluing to the inured surface. Ideally a chitosan gel or fibrinogen gel may be used.

During the healing phase supporting s.c of the factors (EPO, GCSF) can be used. TGF may be reapplied as well.

Example 12

Sphincter Engineering

Sphincters are repaired intraooperatively in a manner comparable to the cardiac engineering. The stem cell/factor gel is injected into the remaining sphincter tissue. In addition a ring of neo-tissue can be formed surrounding the old sphincter. Remodeling occurs in 2 weeks.

Example 13

Venous Valve Engineering

For regeneration of venous valves a stem cell collagen sponge including EPO and/or GCSF is wrapped around the vein intraoperatively. It has a length of 2-3 cm and can be sutured to approximate the insufficient valve. FGF may be used in addition but is not always needed.

Example 14

Vertebral Bone Engineering

The stem cell gel is injected into the collapsed vertebra after repositioning it back to its original size. The gel polymerizes inside. It may be mixed with collagen powders and any form of bone replacement material. A supportive commitment factor is vitamin D. The use of BMP or derivatives is not need but a co-application with the other factor and the stem cell process is possible.

The invention claimed is:

1. A method of preparing an individually engineered implant ex vivo, the implant being a treated scaffold and based on either a natural or a synthetic scaffold which serves as a supporting matrix for tissue generation, wherein the implant is used for treatment of a patient with a tissue defect and a tissue injury, the method comprising the steps:
   (i) providing a natural or synthetic scaffold as a supporting matrix for growth of tissue cells;
   (ii) forming a stem cell preparation with autologous stem cells obtained from an anesthetized patient being treated, wherein the autologous stem cells are obtained from either the bone marrow or peripheral blood;
   iii) forming a healthy cell preparation comprising healthy cells biopsied from the defective and the injured tissue of the anesthetized patient, wherein the healthy cells function either as copy cells or co-differentiating cells supporting local epithelialization and stem cell differentiation in the defective tissue and the injured tissue;
   (iv) incubating the stem cell preparation of step (ii) with a booster composition comprising a boosting factor which stimulates stem cells and accelerates remodeling of tissue cells, wherein the boosting factor is selected from the group consisting of erythropoietin (EPO), thrombopoietin and human growth hormone (hGH);
   (v) loading and injecting the healthy cell preparation of step (iii) either onto or into the scaffold supporting matrix to form a pretreated scaffold matrix;
   vi) incubating the pretreated scaffold matrix of step (v) with the incubated stem cell preparation of step (iv) together with a combined composition comprising
   (a) a native recruitment factor for recruiting and increasing the availability of stem cells, wherein the native recruitment factor is selected from the group consisting of G-CSF and GM-CSF; (b) a native commitment factor that promotes differentiation of stem cells or its progenitor cells, wherein the native commitment factor is selected from the group consisting of TGFβ, VEGF, vitamin C, and vitamin E; and (c) the boosting factor which stimulates stem cells and accelerates remodeling of tissue cells of step (iv) to form the treated scaffold;
   (vii) carrying out steps (iv)-(vi) under sterile conditions in either a bioreactor chamber or a laminar air flow cabinet over a period of less than one hour.

2. The method according to claim 1, further comprising the step of selecting the boosting factor that stimulates stem cells and accelerates remodeling of tissue cells from the group consisting of EPO and hGH.

3. The method according to claim 1, further comprising the step of selecting the native recruitment factor that recruits and increases the availability of stem cells is G-CSF, the native commitment factor that promotes differentiation of stem cells or its progenitor cells is TGFβ, and the boosting factor which stimulates stem cells and accelerates remodeling of tissue cells is EPO.

4. The method according to claim 1, wherein the stem cell population of (ii) is autologous mesenchymal stem cells.

5. The method according to claim 1, further comprising the step of adding autologous peripheral blood derived monocytes (PBMC) during the incubation step of step (vi).

6. The method according to claim 1, further comprising the step of not expanding the autologous stem cells before, by a separate process step.

7. The method according to claim 1, further comprising the step of providing the at least one of the native recruitment factor, the native commitment factor and the boosting factor and the stem cells, and healthy cells to the scaffold by one of a viscose gel-like formulation, a glue-like formulation and a glue-like composition.

8. The method according to claim 1, further comprising the step of providing one of a viscose gel-like formulation, a glue-like formulation and a glue-like composition of the at least one of the native recruitment factor, the native commitment factor and the boosting factor and cells for intraoperative in situ treatment of the freshly implanted scaffold at at least one selected site of the defected tissue and the injured tissue.

9. The method according to claim 1, further comprising the step of completing all steps (I)-(viii) in a same operation theater of the patient.

10. The method according to claim 1, further comprising the step of carrying out the steps (iv)-(vi) under sterile conditions in either the bioreactor chamber or the laminar air flow cabinet over a period of 10 to 30 minutes.

11. An ex vivo method for manufacturing an individually engineered implant based on either a natural or a synthetic scaffold as supporting matrix for a growth of tissue cells for scar free healing and remodeling of either defected or injured tissue in a patient, the method comprising the steps:
   (i) providing a stem cell preparation of freshly prepared autologous non-expanded stem cells obtained from either peripheral blood or bone marrow cells of the patient, wherein the stem cells are stimulated by incubating the stem cell preparation with erythropoietin (EPO);

(ii) providing a healthy cell preparation of healthy cells as copy cells obtained by biopsy from either the defected or the injured tissue of the patient, and incubating the healthy cell preparation with the scaffold thereby loading the healthy cells either onto or into the scaffold;

(iii) incubating the pretreated scaffold of step (ii) with the stem cell preparation of step (i) in a presence of a composition comprising (a) a first native factor which stimulates stem cells, the first native factor being EIPO, (b) a second native factor which recruits the stem cells and increases stem cell availability, the second native factor is either G-CSF or GM-CSF, and (c) a third native factor that promotes differentiation of the stem cells, the third native factor is one of TGFβ, VEGF, vitamin E and vitamin C; and (iv) providing the pretreated, incubated scaffold for implantation into the patient by a surgeon; carrying out the steps (i) to (iv) under sterile conditions in either a bioreactor chamber or a laminar air flow cabinet.

12. The method according to claim 11, further comprising a step of pretreating at least one of the stem cell preparation and the healthy cell preparation by incubating the stem cell preparation with a composition comprising EPO, G-CSF and TGF-β.

13. The method according to claim 11, further comprising a step of incubating the pretreated scaffold in the incubation step (iii) with autologous peripheral blood derived monocytes (PBMC).

14. The method according to claim 11, further comprising a step of providing at least one of the first native factor, the second native factor, the third native factor, the stem cells and the healthy cells to the scaffold by either a viscous gel-like or a glue-like either composition.

15. The method according to claim 14, further comprising a step of obtaining either the gel-like or the glue-like composition by polymerization after addition of either Ca++ or Thrombin.

16. The method according to claim 11, wherein the stem cells are CD90 positive stem cells.

17. The method according to claim 11, wherein the scaffold obtained by step (iv) is treated with either a gel-like or glue-like composition comprising (i) the stem cell preparation of the freshly prepared nonexpanded autologous stem cells (ii) a factor that stimulates stem cells and accelerates remodeling of tissue cells, wherein this factor is EPO, (iii) a factor which recruits and increases availability of stem cell, wherein this factor is either G-CSF or GM-CSF, and (iv) a factor that promotes differentiation of stem cells or its progenitor cells, wherein this factor is TGF-β, VEGF, vitamin C, or vitamin E.

* * * * *